(12) United States Patent
Engel et al.

(10) Patent No.: US 6,167,886 B1
(45) Date of Patent: Jan. 2, 2001

(54) DEVICE FOR TREATMENT OF MALE AND FEMALE URINARY INCONTINENCE

(75) Inventors: Konrad Engel; Kilian Engel, both of Gaissach (DE)

(73) Assignee: Medi-Globe Vertriebs GmbH, Prien (DE)

( * ) Notice: Under 35 U.S.C. 154(b), the term of this patent shall be extended for 0 days.

(21) Appl. No.: 09/384,956

(22) Filed: Aug. 27, 1999

Related U.S. Application Data

(63) Continuation-in-part of application No. 08/864,367, filed on May 28, 1997.

(51) Int. Cl.$^7$ ........................................................ A61F 5/48
(52) U.S. Cl. .................................. 128/885; 128/DIG. 25; 600/29
(58) Field of Search .................... 128/885, 886, 128/DIG. 25; 600/29–31

(56) References Cited

U.S. PATENT DOCUMENTS

| | | | |
|---|---|---|---|
| 3,331,371 | * 7/1967 | Rocchi | 128/DIG. 25 |
| 3,812,841 | * 5/1974 | Isaacson | 128/DIG. 25 |
| 4,014,369 | 3/1977 | Kobres, Jr. . | |
| 4,932,938 | 6/1990 | Goldberg et al. . | |
| 4,946,449 | 8/1990 | Davis, Jr. . | |
| 5,090,424 | 2/1992 | Simon et al. . | |
| 5,112,306 | * 5/1992 | Burton | 128/DIG. 25 |
| 5,234,409 | * 8/1993 | Goldberg | 604/96 |

* cited by examiner

Primary Examiner—Michael A. Brown
(74) Attorney, Agent, or Firm—Thomas I. Rozsa; Tony D. Chen; Jerry Fong

(57) ABSTRACT

A device for treatment of human urinary incontinence in the form of a catheter which can be inserted into the urethra and carries a balloon arrangement which can be filled with fluid to close off the urinary bladder, where the balloon arrangement holds the catheter in the lumen of the bladder. The fluid can be admitted to and discharged from the balloon arrangement via at least one channel running along the catheter wall which is closed off at the distal end of the distal part of the catheter. A self-closing valve is formed at a proximal end of the proximal part of the catheter. A hydraulic actuating mechanism is also located in the lumen of the urinary bladder. The hydraulic actuating mechanism can be hydraulically actuated by mechanical pressure exerted on a compressible balloon located at the distal end of the catheter. The compressible balloon is filled with fluid and is connected to the actuating mechanism via a connecting channel.

43 Claims, 10 Drawing Sheets

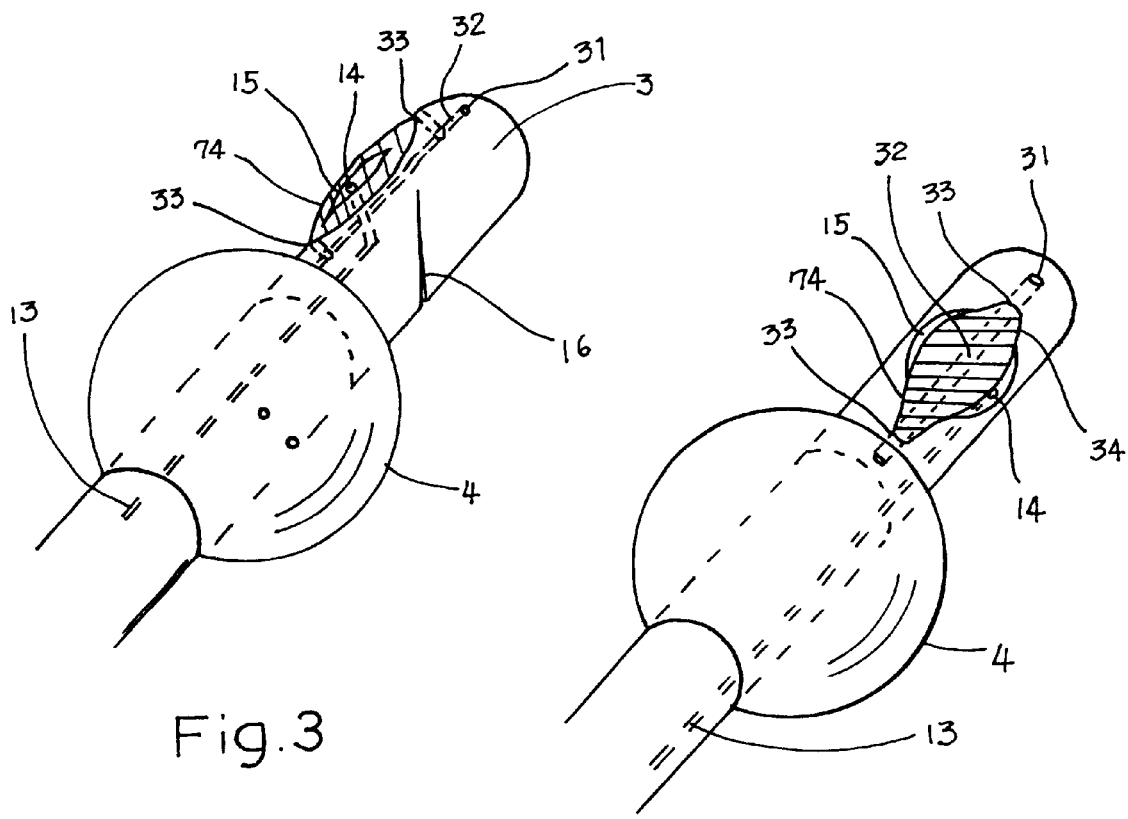
Fig.3
Fig.4
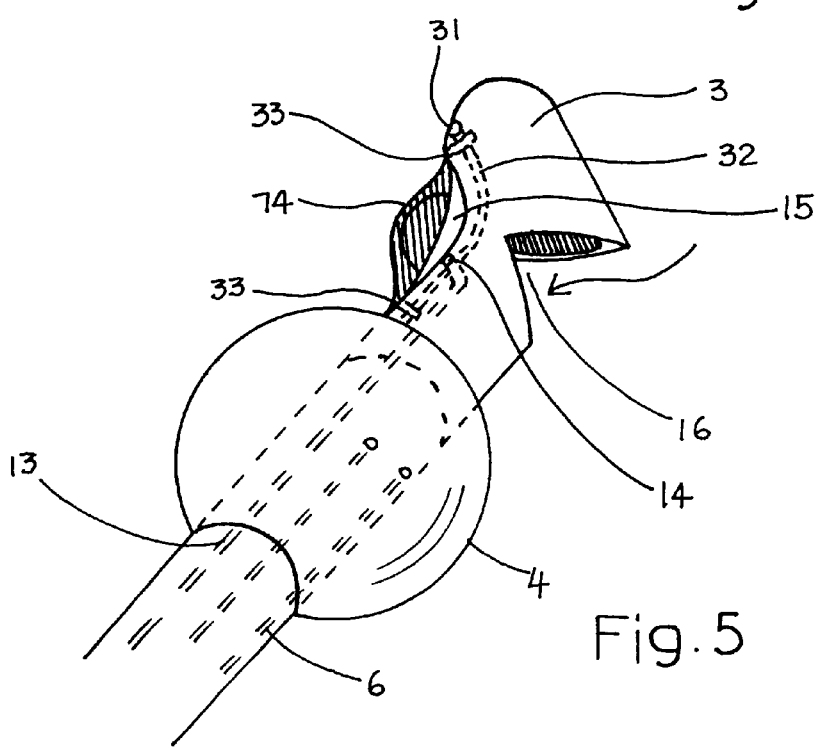
Fig.5

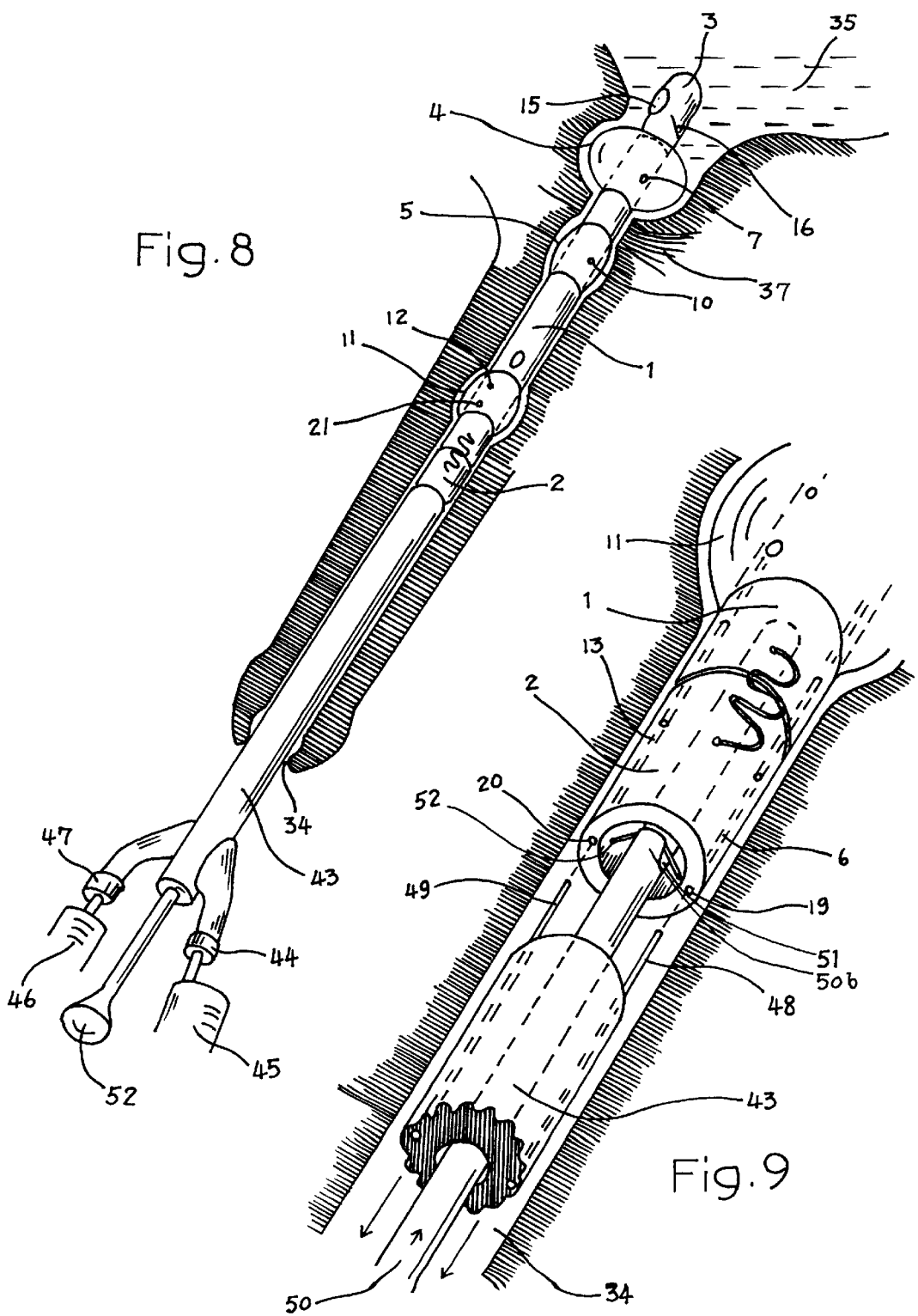

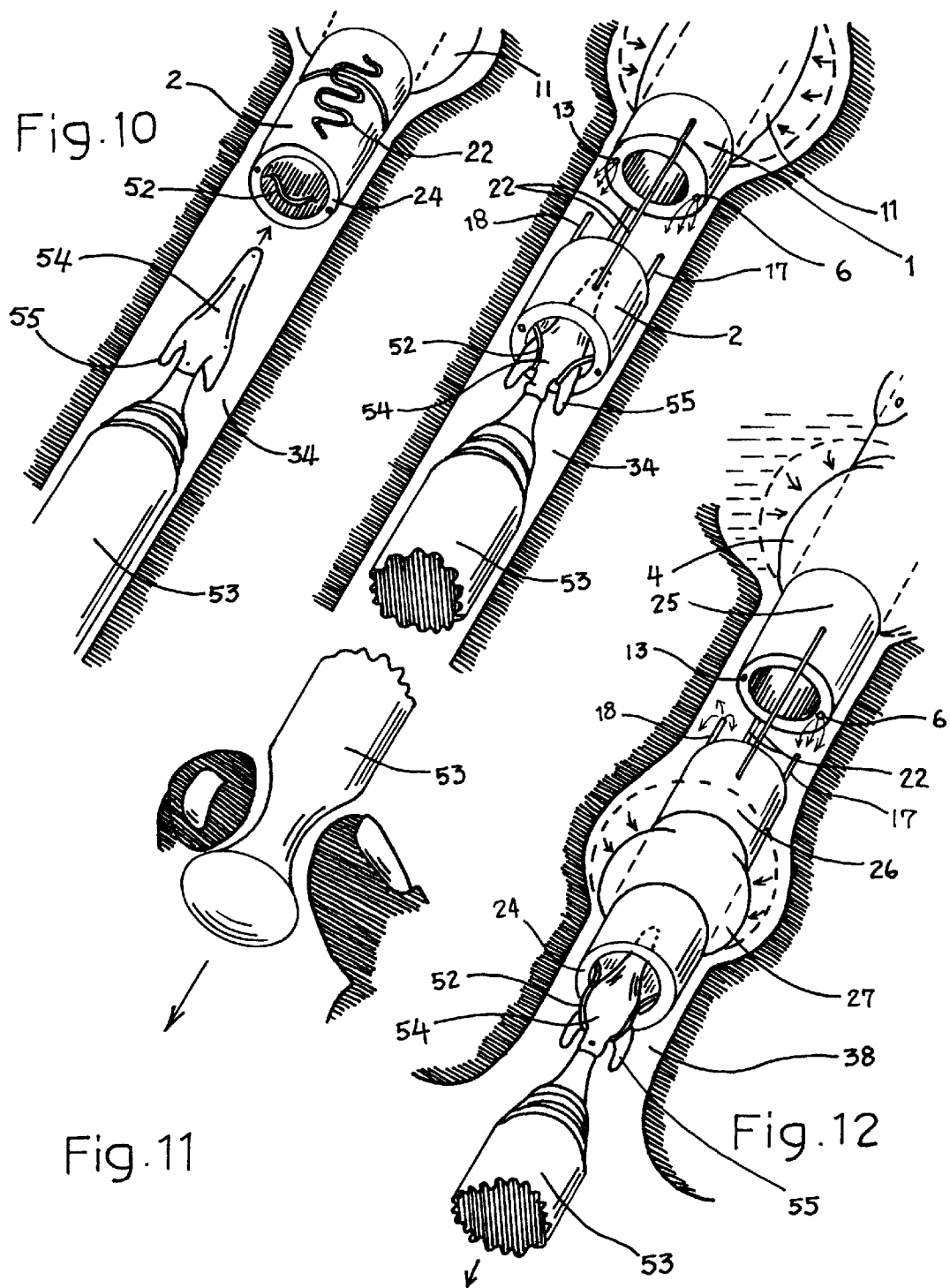

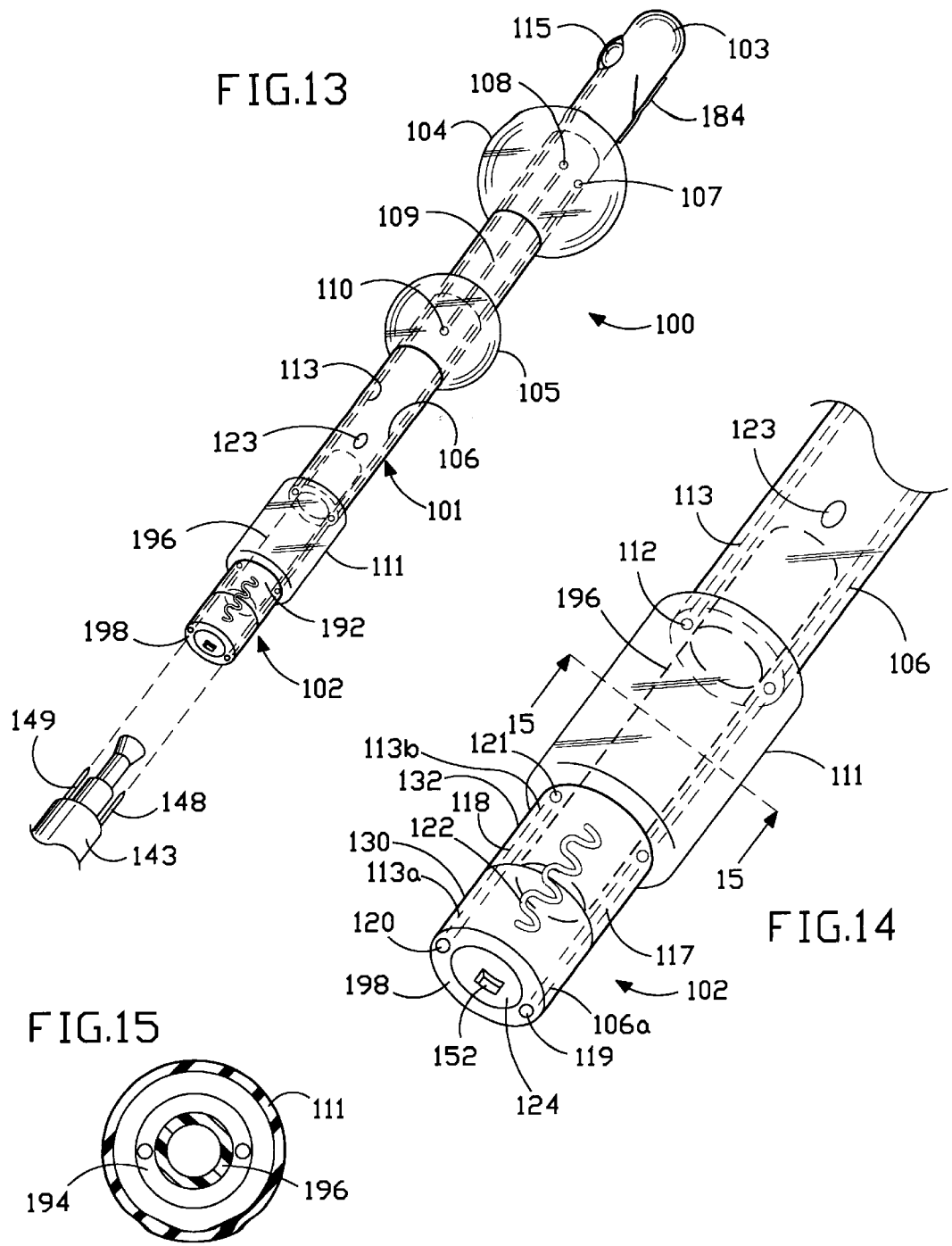

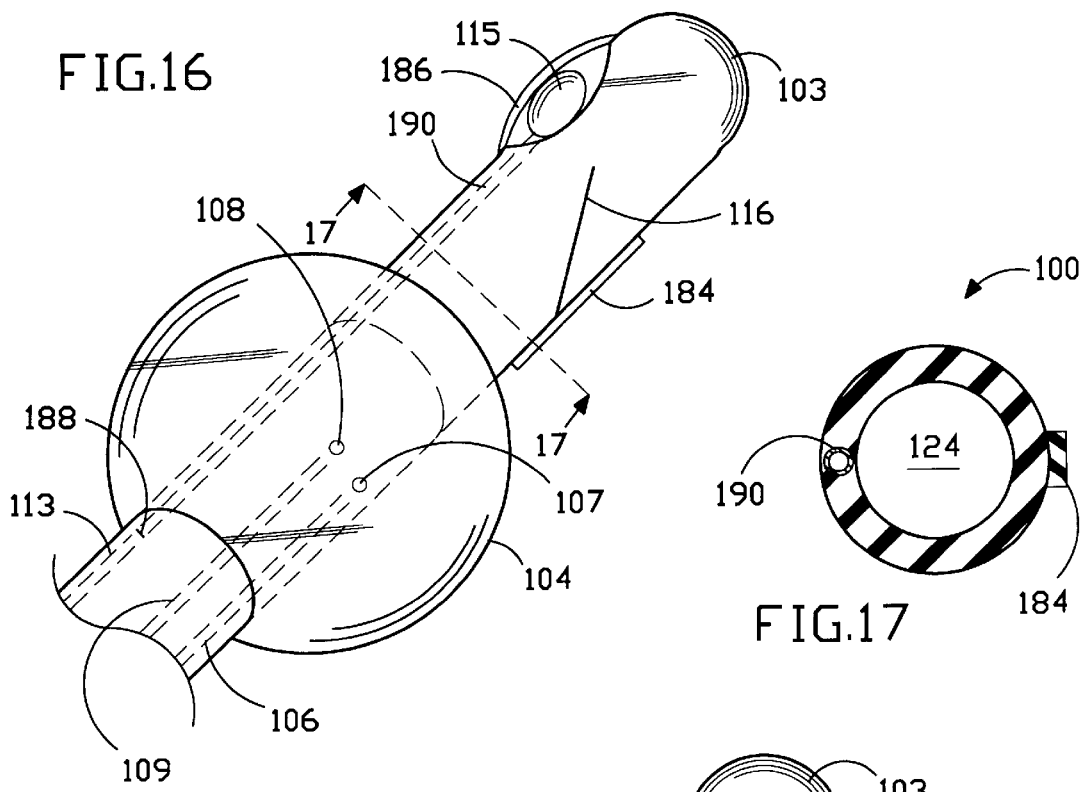
FIG.16
FIG.17
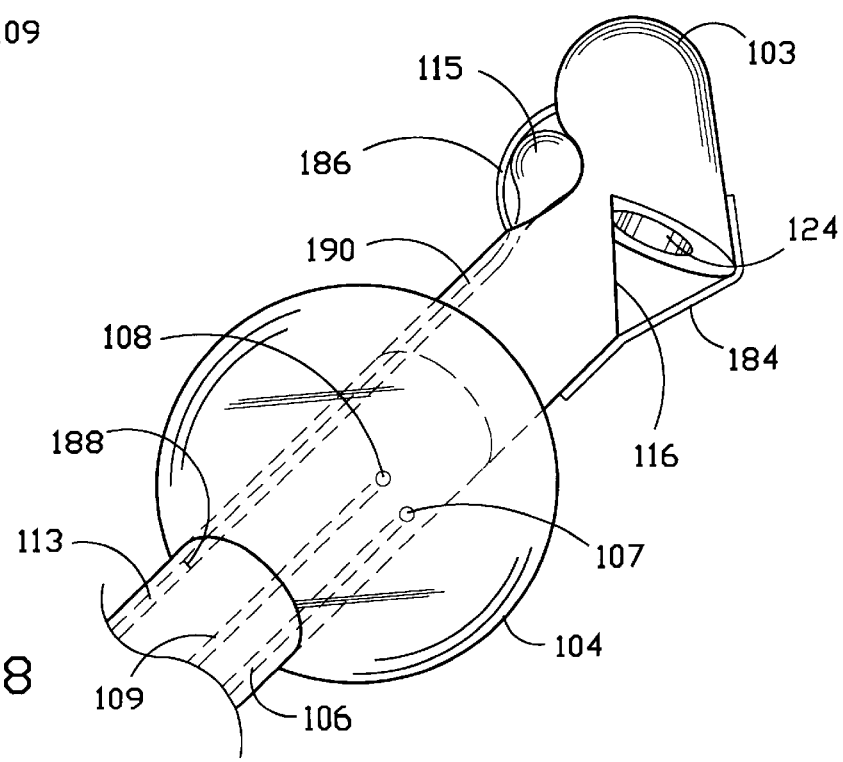
FIG.18

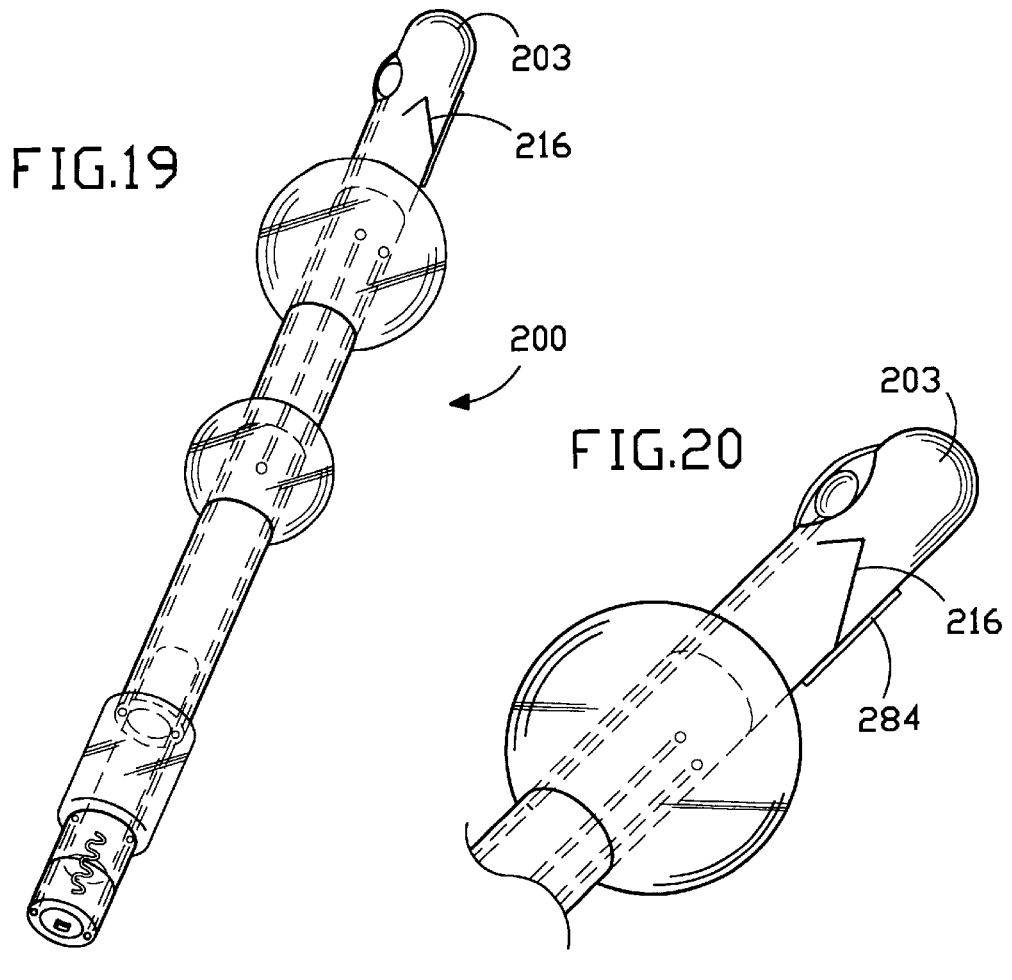
FIG.19
FIG.20
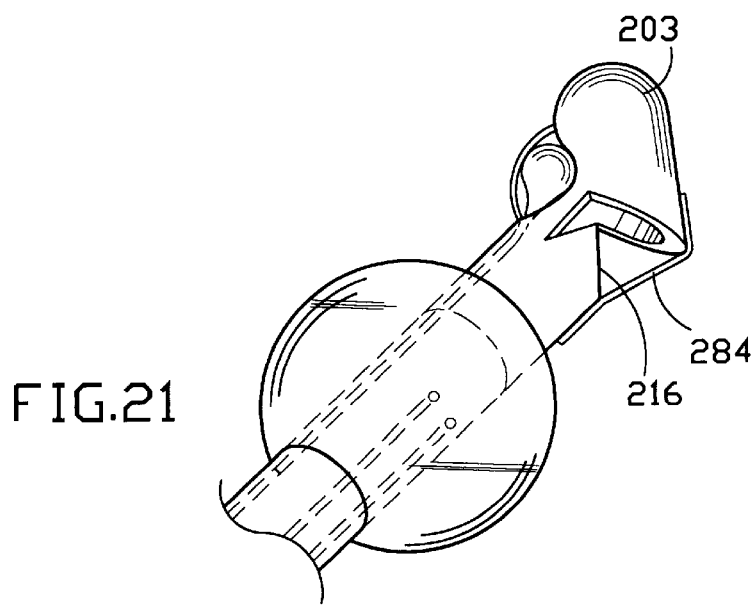
FIG.21

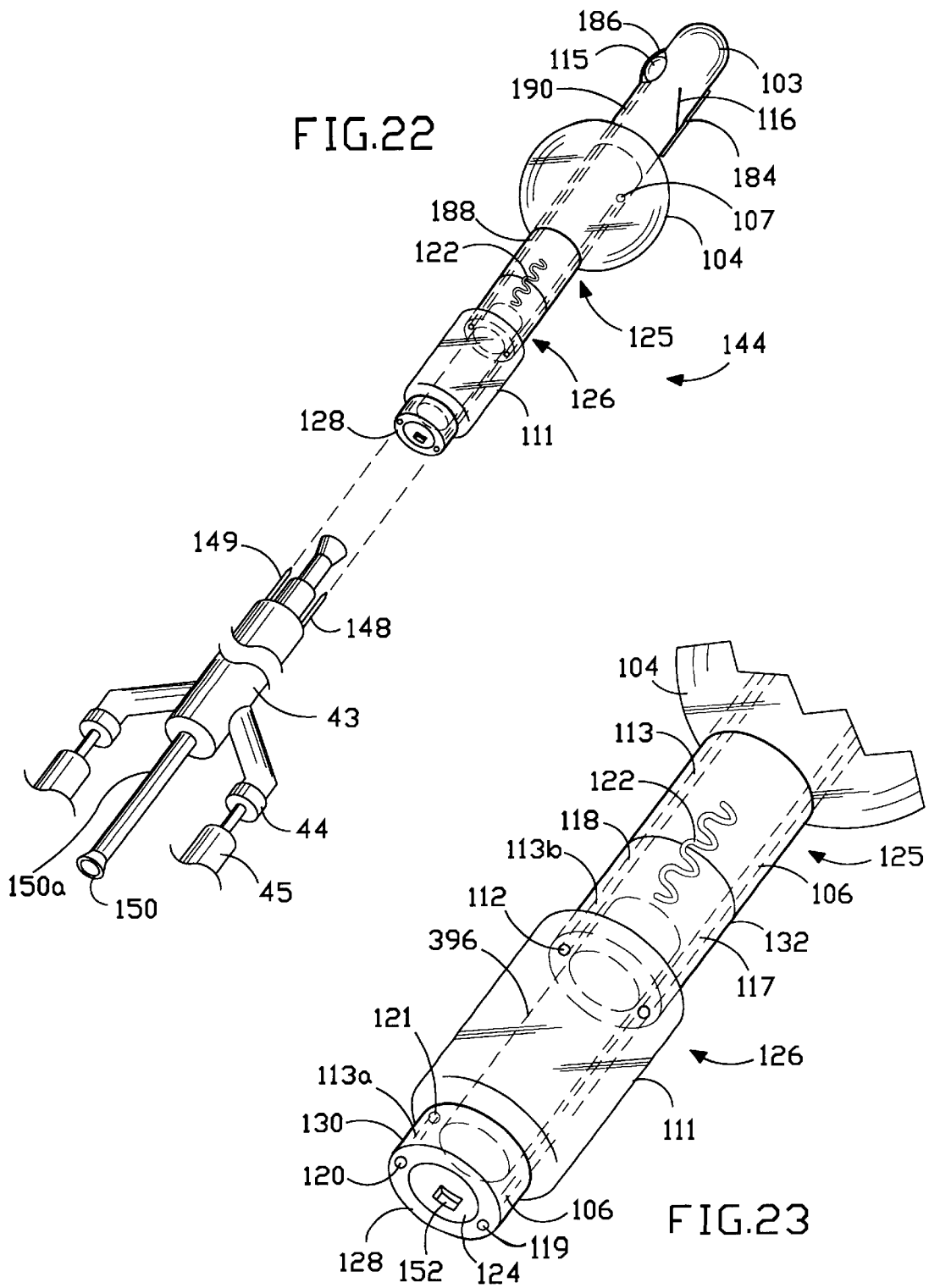

DEVICE FOR TREATMENT OF MALE AND FEMALE URINARY INCONTINENCE

This application is a continuation-in-part of application Ser. No. 08/864,367 filed on May 28, 1997, now pending.

BACKGROUND OF THE INVENTION

1. Field of the Invention

The invention relates to a device for the treatment of male and female urinary incontinence according to the preamble of claim 1.

Urinary incontinence is understood as meaning the involuntary loss of urine from the urinary bladder and urethra. The causes are either direct damage to the occlusive mechanism (sphincter muscle) of the urinary bladder, generally as a result of an operation on the prostate gland or by infiltration of a prostate gland carcinoma in men or a sphincter muscle injury as a result of childbirth in the case of women. Further causes of urinary incontinence are nerve damage resulting form metabolic diseases such as e.g. diabetes mellitus or as a result of traumas to the nerves to the urinary bladder and its occlusive mechanism such as stroke, tumor operations in the pelvic region or injuries to the spinal cord.

In the case of incontinence due to nerve damage, the occlusive mechanism of the bladder can normally no longer be sufficiently opened so that the loss of urine (incontinence) occurs only after maximum filling of the urinary bladder, and even after elimination, the bladder is not completely empty. Therefore, the excretion of urine occurs uncontrollably and without completely emptying the volume of the bladder. The consequences are not only the urination but also an over-expansion of the urinary bladder and in many cases the reflux of urine up to both kidneys with subsequent kidney damage. The various forms of incontinence generally affect people of advanced age.

2. Description of the Prior Art

A wide range of different methods are already known for treating and overcoming the urinary incontinence, depending on the cause of the incontinence and the sex of the patient; in serious cases, however, these are generally not sufficiently effective or require an operation with or without implantation and is not free from disadvantages in all cases.

In the case of incontinence due to a partial or complete loss of function of the occlusive mechanism of the urinary bladder, particularly in the case of the man, use of a surgically implantable "Scott" artificial bladder sphincter muscle is known (AMS 800 from Messrs American Medical Systems) and can be used. The implant is very expensive and should only be implanted by experienced surgeons. Serious infections or necroses of the tissue surrounding the implant caused by pressure necessitating the removal of the implant again have been repeatedly observed. In women, this form of incontinence can frequently be successfully treated by physical therapy or by a less serious operation without implant.

A further known device for overcoming male incontinence consists of a penis clamp or penoring by which pressure from outside exerts a more or less traumatizing pressure on the penis or urethra. Furthermore there is a risk of slipping in the underwear with subsequent urination.

Furthermore, urine collecting systems worn outside the body with urine bag (urinal) or absorbent media (disposable napkins) are known for both sexes which serve to collect the urine; these result in skin irritation due to the urine, unpleasant odor and thus social isolation.

Furthermore, a device for female incontinence is known by which the urinary bladder is emptied via a short catheter protruding out of the urethra by manual actuation of a valve located in the vestibule of the vagina (EP 0407 218 A1). The valve located in the vestibule of the vagina can lead to a colonization of the device with bacteria from the vestibule of the vagina.

More recently, a device for female incontinence has come onto the market under the name "Reliance TM" (U.S. Pat. No. 5,090,424) which consists of an inflatable urethra insert which has to be completely removed several times a day before each emptying of the bladder rather like a tampon and subsequently has to be replaced by a new device, thus making it very costly.

Finally, devices for male incontinence are known with which many of the disadvantages outlined above can basically be avoided (U.S. Pat. No. 4,946,449, DE-OS 4,014, 369=U.S. Pat. No. 4,932,938, EP-A 0,265,207, EP 0,543, 309 B1). These known devices consist essentially of a catheter which is inserted into the male urethra and carries a balloon at its proximal end which can be filled with a fluid (e.g. water) and thus expanded. This balloon closes off the urinary bladder at the entry to the urethra and prevents the catheter from unintentionally slipping out. There is a second balloon which is positioned at a distance from the first balloon. The second balloon is closer to the distal end than the first balloon. The second balloon can be filled with fluid which, when the catheter is in the fitted condition, the second balloon lies outside the bladder sphincter muscle in the urethra and thus prevents the catheter from unintentionally slipping further into the bladder. The length of the catheter is such that when inserted its distal end is completely contained in the penis; a valve is located in the distal end section which can be felt through the wall of the urethra in the penis area. The valve is for example a crocodile valve, lip valve, ball valve or slit valve whose normally closed condition can be changed to the open position by the pressure of the two fingers so that urination is possible. These known valves located in the distal end section of the catheter have several serious disadvantages. The maximum lumen cross-section of a catheter is 5–6 mm which makes the production of lip or crocodile valves miniaturized to these dimensions difficult or even impossible at reasonable cost. A liquid pressure of up to 100 cm water column is exerted on the closed valve in opening direction by the pressure inside the bladder so that the danger of the valve tipping outward with subsequent loss of function is practically unavoidable. The silicone material used almost exclusively for long term catheters has only a relatively low rubbery-elastic resilience so that lip valves and crocodile valves made of this material require a metal-elastic spring device to return the open valve into a sealing closed position. The production of this spring device in the small dimensions in question here is also technically very complicated. Metallic devices in the catheter wall also result in a hardening of the wall and increase the danger of pressure-related damage to the delicate urethra mucosae. All the above-mentioned valves fitted to the distal end of the catheter result in a significant loss of catheter lumen. This applies in particular to ball valves and slit valves so that no adequate flow of urine is assured in open condition with these valve types. Non-deformable valve elements such as e.g. balls tend to become considerably encrusted due to the substances dissolved in the urine.

SUMMARY OF THE PRESENT INVENTION

The task of the invention is therefore to design a device for treatment and remedying in particular of the male incontinence of the type described at the beginning in such a way that the catheter valve is easy to manufacture, closes reliably with adequate elastic resilience, does not open accidentally even under high pressure inside the bladder, leaves the catheter lumen effectively free in its complete cross-section for free drainage of the urine from the bladder and the insertion of the device into the urethra and its removal from the urethra is simple. In addition, the device should be suitable in its basic principle, but after adaptation to the different anatomical situation of the woman, also for treatment and remedying of the female urinary incontinence.

According to the invention, this task is solved with a device of the type described at the beginning by designing the device in accordance with the characterizing part of claim 1.

The device to which the invention relates is an incontinence catheter which can be completely inserted into the urethra with two sealing balloons, whereby the valve closing off the catheter is located at the proximal end of the catheter extending into the urinary bladder. The valve is opened by finger pressure on an additional balloon filled with fluid (e.g. water) at the distal end of the catheter which can be felt through the wall of the urethra and which is connected to the valve at the proximal end of the catheter by a channel in the catheter wall. The design features of this valve, which can be opened and closed by a hydraulic mechanism, correspond to no previously known catheter valve and, when the valve is open, lead to no reduction in the drainage lumen of the catheter so that an adequate urinary stream is assured. The miniaturization of a catheter valve to the size of the inner cross-section of the catheter and the associated difficulties in the industrial manufacturing are eliminated. The valve is closed automatically by a simple elastic mechanism when the finger pressure is released from the distal catheter balloon. In addition, the leak-tightness of the closed valve is increased by high pressure inside the bladder.

The attachment of the valve to the proximal end of the catheter as provided for by the invention allows a modified form to be used for women as a completely concealed incontinence catheter with no connection to the body surface for the first time, whereby the occurrence of an infection of the urinary bladder rising from the vestibule of the vagina regularly observed with catheters or external catheter valves can be avoided.

The insertion and positioning as well as the filling of the catheter balloons with a fluid (e.g. water) is performed using a special disposable, sterile insertion rod.

The removal of the incontinence catheter from the urethra is performed using a further disposable, specially formed sterile rod which separates the distal part of the catheter from the proximal part so that the fluid (e.g. water) escapes from the balloons. In principle, the removal of the incontinence catheter from the urethra can also be performed visually through a cystoscope using a conventional urethral foreign-body forceps.

Both the male and the female incontinence catheters are therefore made of a relatively simple construction, the technically almost impossible miniaturization of a valve housed in the distal catheter lumen is eliminated so that the incontinence catheters can be manufactured inexpensively as disposable articles. No previously unknown technical processes are required for production. The potential materials are physiologically safe, silicone or latex-based polymers, possibly also with a prior-art hydrophilic silver coating or silver coating as additional protection against bacterial colonization and good compatibility with the mucosae and a monofilament surgical thread material. It is therefore possible to leave the catheter in the lower urinary tract for several weeks or even months.

Alternatively, the invention is a male incontinence catheter which can be completely inserted into the urethra with two sealing balloons, whereby the catheter valve is located at the proximal end of the incontinence catheter and extends into the urinary bladder. The catheter valve is opened by finger pressure on an additional actuating balloon which is filled with fluid (e.g. water) at the distal end of the incontinence catheter. The additional balloon can be felt through the wall of the urethra and is connected to the catheter valve at the proximal end of the catheter by a channel in the catheter wall. The design features of this valve which can be opened and closed by a hydraulic mechanism correspond to no previously known catheter valve and, when the valve is open, it leads to no reduction in the drainage of the lumen of the catheter so that an adequate urinary stream is assured. The miniaturization of the catheter valve to the size of the inner cross-section of the catheter and the associated difficulties in the industrial manufacturing are eliminated. The valve is closed automatically by a simple elastic mechanism when the finger pressure is released from the distal catheter balloon. In addition, the leak-tightness of the closed valve is increased by high pressure inside the bladder and a small narrow elastic strip (which can be made of silicone, rubber, or other elastic material) which is attached onto the catheter in the longitudinal direction and crosses over the slit or opening in the catheter valve to keep the catheter valve tightly closed.

Further alternatively, the invention is a male incontinence catheter which can be completely inserted into the urethra with two sealing balloons, whereby the catheter valve is located at the proximal end of the incontinence catheter and extends into the urinary bladder. The catheter valve is generally an angled valve cut at the proximal end. The catheter valve is opened by finger pressure on an additional actuating balloon which is filled with fluid (e.g. water) at the distal end of the incontinence catheter. The additional balloon can be felt through the wall of the urethra and is connected to the catheter valve at the proximal end of the catheter by a channel in the catheter wall. The design features of this valve which can be opened and closed by a hydraulic mechanism correspond to no previously known catheter valve and, when the valve is open, it leads to no reduction in the drainage of the lumen of the catheter so that an adequate urinary stream is assured. The miniaturization of the catheter valve to the size of the inner cross-section of the catheter and the associated difficulties in the industrial manufacturing are eliminated. The valve is closed automatically by a simple elastic mechanism when the finger pressure is released from the distal catheter balloon. In addition, the leak-tightness of the closed valve is increased by high pressure inside the bladder and a small narrow elastic strip (which can be made of silicone, rubber, or other elastic material) which is attached onto the catheter in the longitudinal direction and crosses over the slit or opening in the catheter valve to keep the catheter valve tightly closed.

Also further alternatively, the invention is a female incontinence catheter which can be completely inserted into the urethra with one sealing balloon, whereby the catheter valve is located at the proximal end of the incontinence catheter and extends into the urinary bladder. An index finger is inserted into the vagina which in turn actuates an actuating balloon by pressing the actuating balloon against the symphysis. The actuating balloon also functions at the same time as a second sealing balloon. By this pressure, a tiny actuating balloon is filled with fluid and the catheter valve is opened. The design features of this valve which can be opened and closed by a hydraulic mechanism correspond to no previously known catheter valve and, when the valve is open, it leads to no reduction in the drainage of the lumen of the catheter so that an adequate urinary stream is assured. The miniaturization of the catheter valve to the size of the inner cross-section of the catheter and the associated difficulties in the industrial manufacturing are eliminated. The valve is closed automatically by a simple elastic mechanism when the finger pressure is released from the distal catheter balloon. In addition, the leak-tightness of the closed valve is increased by high pressure inside the bladder and a small narrow elastic strip (which can be made of silicone, rubber, or other elastic material) which is in attached onto the catheter in the longitudinal direction and crosses over the slit or opening in the catheter valve to keep the catheter valve tightly closed.

Further novel features and other objects of the present invention will become apparent from the following detailed description, discussion and the appended claims, taken in conjunction with the drawings.

DESCRIPTION OF THE PRIOR ART

One embodiment for the male and the female urethra is explained in further detail below on the basis of the attached drawings. The drawings show:

FIG. 3 is a schematic view of the identical male and female proximal catheter end with closed valve as a side view.

FIG. 4 is a schematic view of the identical male and female proximal catheter end with closed valve, looking towards the side opposite the valve opening.

FIG. 5 is a schematic view of the identical male and female proximal catheter end with open valve as a side view.

FIG. 8 is a schematic view of the male incontinence catheter with attached insertion rod in the male urethra during the balloon filling phase.

FIG. 9 is a schematic view of the distal section of the male incontinence catheter in the male urethra at the moment of disconnection of the insertion rod.

FIG. 10 is a schematic view of the distal section of the male incontinence catheter in the male urethra during the insertion of the special rod-like extraction device.

FIG. 11 is a schematic view of the distal section of the male incontinence catheter in the male urethra at the beginning of the extraction using the extraction device.

FIG. 12 is a schematic view of the distal section of the female incontinence catheter in the female urethra at the beginning of the extraction using the extraction device.

FIG. 13 is a schematic view of an alternative embodiment of the present invention male incontinence catheter with a partial illustration of an insertion rod.

FIG. 14 is an enlarged schematic view of the catheter distal part of the present invention male incontinence catheter.

FIG. 15 is an enlarged cross-section view taken along line 15—15 of FIG. 14.

FIG. 16 is an enlarged side elevational view of the proximal end of the present invention male or female incontinence catheter with the catheter valve in the closed condition.

FIG. 17 is an enlarged cross-section view taken along line 17—17 of FIG. 16.

FIG. 18 is an enlarged side elevational view of the proximal end of the present invention male or female incontinence catheter shown in FIG. 13, with the catheter valve in the open condition.

FIG. 19 is a schematic view of another alternative embodiment of the present invention male incontinence catheter with a partial illustration of an insertion rod.

FIG. 20 is a schematic view of the proximal end of the present invention male or female incontinence catheter shown in FIG. 19, with the catheter valve in the closed condition.

FIG. 21 is a schematic view of the proximal end of the present invention male or female incontinence catheter shown in FIG. 19, with the catheter valve in the open condition.

FIG. 22 is a schematic view of another alternative embodiment of a female incontinence catheter with a partial illustration of an insertion rod.

FIG. 23 is an enlarged schematic view of the catheter distal section of the female incontinence catheter.

In the drawings, the same reference symbols have been used for components and characteristics which are identical in the various design forms.

Figure 1:
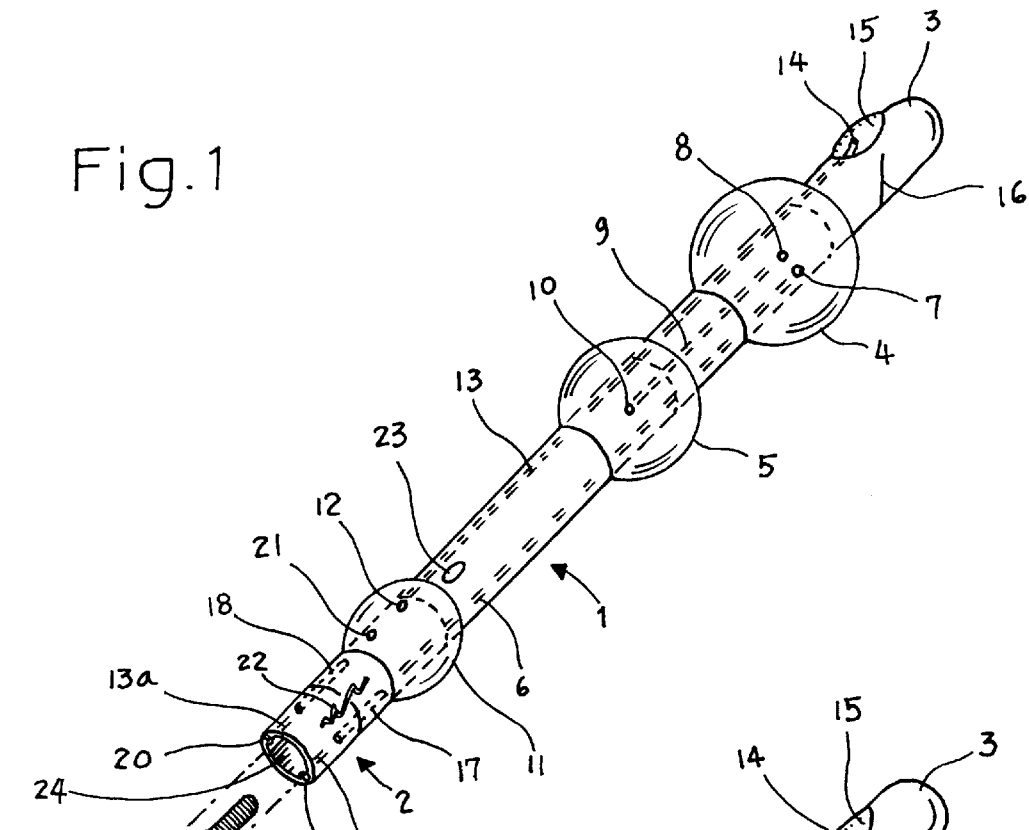
FIG. 1 is a schematic view of the male incontinence catheter with partial illustration of the insertion rod.

FIG. 1 shows the male incontinence catheter drawn approximately in the scale 1:1, made of elastic material, e.g. silicone. The proximal end of the catheter carries a balloon 4 with a capacity of about 10 ccm. Another balloon 5 which has a capacity of about 2–3 ccm is located at a short distance distally to it. A channel 6 which runs longitudinally in the wall of the catheter ends with an opening 7 within the balloon 4. Balloon 4 is connected with balloon 5 by another opening 8 and a short longitudinal channel 9 along the catheter wall and another opening 10. The opening 10 has a smaller cross-section than the openings 7 and 8 as a result of which, balloon 5 fills more slowly with fluid in comparison to balloon 4.

At the distal end of the proximal catheter section 1 is a third balloon 11 with a capacity of about 2 ccm. The opening 12 of the catheter wall connects this balloon 11 by a longitudinal channel 13 along the catheter wall and an opening 14 with a small semi-balloon 15 (capacity: 0.5–1 ccm) at the proximal end 3 of the catheter. This semi-balloon 15 is part of the hydraulic mechanism which opens and closes the opening 16 of the valve that drains the urinary bladder. This opening 16 is made by a diagonal cut into the wall of the proximal end 3 of the catheter. In a closed position, the sealing edges of the openings 16 have to be waterproof.

The two catheter sections 1 and 2 are connected by two small plastic pipes 17 and 18. Additionally, the plastic pipe 17 connects the longitudinal channel 6 with an "elastic puncture valve" 19 at the front side of catheter section 2. Channel 13 has three parts. In addition to the first part which connects opening 12 to opening 14 as discussed above, channel 13 starts at puncture valve 20 and is connected to opening 21 within balloon 11 through plastic pipe 18 which bridges the parts of channel 13 running from puncture valve 20 to the portion of channel 13 connected to opening 21 within balloon 11. This opening 21 has a wider cross-section than the other opening 12 within balloon 11 in order to avoid overfilling and overstretching of semi-balloon 15 when filling balloon 11 with fluid. When parts 1 and 2 are disconnected, pipes 18 and 17 remain with the portions of their respective channels that are in part 2.

Parts 1 and 2 are attached together by a pair of threads 22 (only one is shown) such that the ends of the threads 22 attach parts 1 and 2 together so that a portion of the threads remain loose. When it is desired to remove the catheter from the urethra, part 2 is pulled away from part 1 (see FIGS. 11 and 12). At that time, water from balloons 4, 5 and 11 can empty from channels 13 and 6 so that the catheter can then be removed from the urethra. The person pulls on part 2 and since part 2 and part 1 are connected together by the threads, it is possible to remove the entire catheter by pulling only on part 2.

Proximally to the distal balloon 11, the catheter wall has two big holes 23 to drain the secretion produced by urethral glands. Besides this, there is a cross-wise running thread 52 according to FIG. 9 and FIG. 10 attached to the inside of lumen 24 of the distal catheter section 2. This thread 52 is necessary for the insertion and extraction of the catheter into, or out of the urethra by means of an external device.

Figure 2:
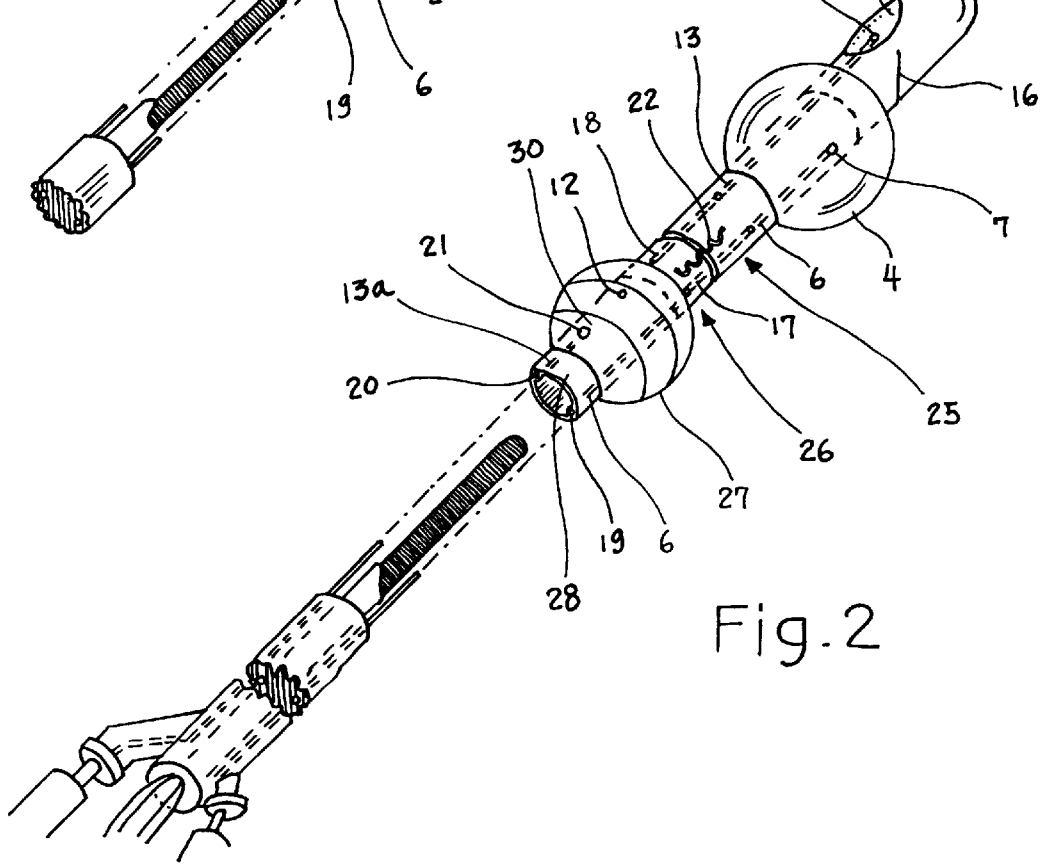
FIG. 2 is a schematic view of the female incontinence catheter with partial illustration of the insertion rod.

FIG. 2 shows the female incontinence catheter drawn approximately in the scale of 1:1, but the distance between the two balloons 4 and 27 should be as short as possible (e.g. 1 cm or less), therefore being shorter than shown in FIG. 2. This detail shortens the whole length of the female catheter. The catheter is put together by two disconnectable sections, a proximal section 25 and a distal section 26. The proximal section 25 carries the first balloon 4 with a capacity of 5–8 ccm. From the distal end 28 of the catheter a longitudinal channel 6 runs to an opening 7 within the proximal balloon 4. A second balloon 27 is located at the distal section 26 which is connected to a small semi-balloon 15 (capacity: 0.5–1 ccm) at the proximal end 3 by an opening 12, a channel 13 and an opening 14. Balloon 27 has a capacity of 2–3 ccm. Semi-balloon 15 is the main part of the hydraulic mechanism which actuates the opening 16 of the valve.

The distal catheter section 26 is again connected to the proximal section 25 by two small plastic pipes 17 and 18. While described as two small plastic pipes 17 and 18, the pipes 17 and 18 can be made of any suitable material including steel or other synthetic material. Plastic pipe 17 connects channel 6 with an "elastic puncture valve" or ball valve 19. Plastic pipe 18 bridges channels 13 and 13a. Balloon 27 fills through an "elastic puncture valve" or ball valve 20 over channel 13a and an opening 21. The opening 21 has again a wider cross-section than the opening 12 within balloon 27.

Figure 7:
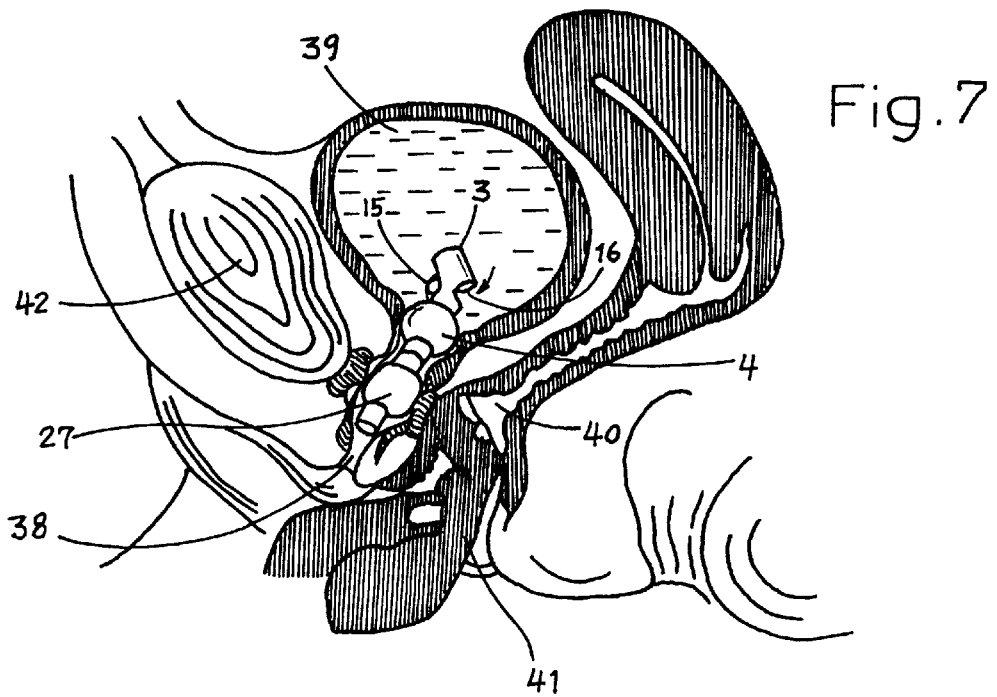
FIG. 7 is a schematic view of the female incontinence catheter to which the invention relates in the female urethra with the valve open.

The surface of balloon 27 has molded into the surface two to four cross-wise running ribs or batons numbered 30 in FIG. 2, or comparable retaining means, to prevent dislocation of the female incontinence catheter inside the short female urethra 38, when balloon 27 is compressed according to FIG. 7. The ribs or comparable retaining means are molded into the exterior surface of the balloon to give the surface a rough texture to prevent dislocation in the urethra.

FIGS. 3, 4 and 5 show details and function of the valve at the proximal end 3 of the catheter, which is the same in both the male and female incontinence catheter. Inside the wall of the proximal end 3 is a resilient elastic plastic baton 32 (similar to a fish bone) which is put in its position through a hole 31 within the catheter tip 3. Two threads 33 are tied around the two ends of baton 32 which attach a rombic-shaped piece of non-elastic tissue 74 to the baton 32. This piece of tissue 74 covers semi-balloon 15 rather tightly. The small semi-balloon 15 fills when pressure is exerted on balloon 11 of the male incontinence catheter according to FIG. 1 and on balloon 27 of the female incontinence catheter according to FIG. 2. In this moment tissue 74, which covers semi-balloon 15 causes traction on both ends of baton 32. Baton 32 bends towards semi-balloon 15 like a hunting bow. Opening 16 of the valve opens and drains the urinary bladder through the lumen of the catheter. When the bladder is empty, the pressure on balloon 11 according to FIG. 1, respectively on balloon 27 according to FIG. 2 is removed and the small semi-balloon 15 collapses. The resilient elastic force of baton 32 allows the tip 3 of the catheter to return to its original shape and thereby closes valve 16.

Figure 6:
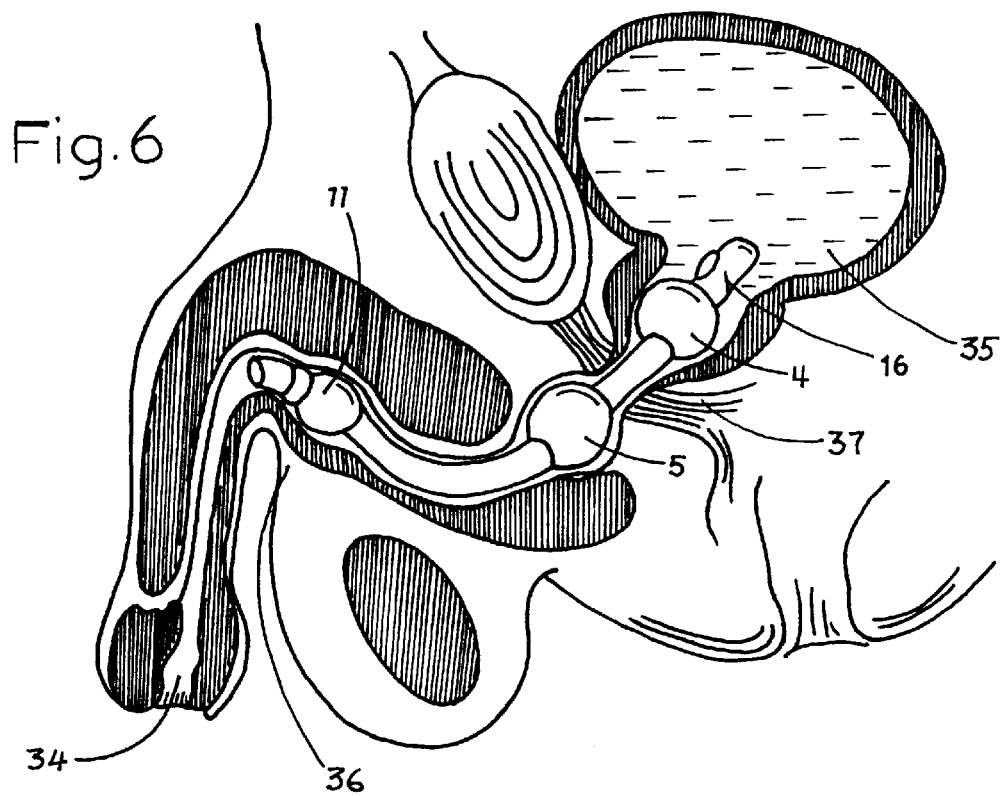
FIG. 6 is a schematic view of the male incontinence catheter to which the invention relates in inserted position in the male urethra, whereby the catheter valve extending into the urinary bladder is closed.

FIG. 6 shows a simplified drawing of the anatomy of the male urethra 34 with a full urinary bladder 35 and a male incontinence catheter according to FIG. 1 with a closed valve 16.

FIG. 7 shows a simplified drawing of the anatomy of the female urethra 38 and a full urinary bladder 39 with a female incontinence catheter according to FIG. 2. An index finger 41 is inserted into the vagina 40 which in turn actuates mechanical pressure on balloon 27 by pressing balloon 27 against the symphysis 42 (which is part of the bones of the pelvis). By this pressure semi-balloon 15 is filled and valve 16 is opened.

FIG. 8 shows a simplified version of the male incontinence catheter according to FIG. 1 in the moment of the insertion of the catheter into the male urethra 34 with a special, rigid, sterile insertion rod 43 which is connected to the catheter. In this simplified version, channel 9 is eliminated and opening 10 is also in channel 6 but opening 10 is much smaller than opening 7 so that as fluid is flowing through channel 6, balloon 4 fills more rapidly than balloon 5.

The insertion rod 43 has two normal catheter valves 44 and 47 at its distal end. Balloon 4, which seals the bladder is already filled with fluid with help of a normal syringe 45 attached to valve 44, and is set into the right position above the sphincter muscle 37 by light traction on the insertion rod.

After positioning the catheter correctly, balloon 11 is filled with fluid with the help of a syringe 46 which is attached to valve 47 of the insertion rod 43. To avoid overfilling and straining of semi-balloon 15 and valve 16, the opening 21 has a wider cross-section than the opening 12, both of which are inside balloon 11. (If balloon 11 is filled gently with fluid it may be possible to do away with one of the openings within balloon 11).

FIG. 9 shows a partial view of the distal section of the male incontinence catheter according to FIG. 1 in the male urethra 34 in the moment of disconnection of the insertion rod 43. Inside the insertion rod 43 is a longitudinal, shiftable, rigid nucleus 50 which protrudes so far into the distal end of the catheter that section 1 and section 2 are stabilized and do not become disconnected when the catheter is inserted into the urethra 34. The proximal end 50b of the nucleus 50 has a semi-circular cross section and a notch 51. This notch 51 holds a thread 52, which is attached diagonally in the lumen of the distal section 2 of the catheter. This is necessary to keep the catheter in its position within the urethra 34 while removing the insertion rod 43. After the outer shell of the insertion rod 43 with its two cannulas 48 and 49 has been retracted slightly, the whole insertion rod 43 can be removed.

The female incontinence catheter according to FIG. 2 is inserted in the same way except that the insertion rod is somewhat shorter.

FIG. 10 and FIG. 11 show a partial view of the removal of the male catheter according to FIG. 1 out of the male urethra 34 with a special, sterile, rigid extraction rod 53. This extraction rod 53 with its harpoon-like rounded proximal tip 54 is inserted blindly into the urethra 34 and into the open lumen 24 of the distal section 2 of the catheter. When removed, the harpoon-like tip 54 catches with its two to four barbs 55 the thread 52 which is attached diagonally in the lumen 24. Further removal of the extraction rod 53 causes a disconnection of section 1 and 2, and a removal of the small plastic pipes 17 and 18 out of the channels 6 and 13. The fluid streams out of the channels and out of the balloons 4, 5 and 11 according to FIG. 1.

The two threads 22 keep a loose connection between section 1 and section 2, so that the whole catheter can be totally extracted out of the urethra 34 by further traction of the extraction rod 53.

FIG. 12 shows a partial view of the removal of the female catheter according to FIG. 2 out of the female urethra 38.

The extraction rod 53 has the same construction as shown in FIGS. 10 and 11, but somewhat shorter. The technique of the removal of the female catheter is the same as shown in FIGS. 10 and 11 with one important difference. By the fact that the female urethra 38 has a wider cross-section than the male urethra, it is possible to retract the full balloon 27 slightly up to the point till the sections 25 and 26 are disconnected and the small pipes 17 and 18 are removed out of the channels 6 and 13. The fluid streams out of the channels and out of the balloons 27 and 4 according to FIG. 2. By further traction of the extraction rod 53 the catheter is extracted totally out of the urethra 38. (The plastic pipes 17 and 18 of the female catheter should be rather short so that a gentle traction at the beginning is sufficient to disconnect the two sections 25 and 26).

The distal hydraulic balloon 11 according to FIG. 1 and 27 according to FIG. 2 have a rather low capacity of 2–3 ccm. If these balloons have a flat oval shape, it might be possible to fill these balloons with fluid during the manufacturing. By doing this, the catheters, both male and female, could be inserted with a "closed hydraulic system". This would enable a simplified method of production. The cross-section of the "hydraulic balloons" 11 and 27 with fluid should not be wider than 22 F for the male, and 24 F or wider for the female catheter, where F is the medical dimension French.

DESCRIPTION OF THE PREFERRED EMBODIMENT

In accordance with FIG. 1, the device to which the invention relates consists of a hose-like or tubular catheter consisting of a proximal part 1 and a distal part 2, which can be removed from the proximal part, both e.g. of silicone, the length of which is so dimensioned that in the inserted condition its distal part 2 lies within the male urethra 34 (FIG. 6) while its proximal end 3 extends into the lumen of the urinary bladder 35 (FIG. 6). In the vicinity of the proximal end 3, a first balloon 4 is permanently attached to the outside of catheter part 1. A short distance distally from it, a second (smaller) balloon 5 is fixed to the outside of catheter part 1. From the distal end of catheter part 2, a channel 6 (shown in dotted lines) runs through the wall of part 2 and of part 1 which ends inside the proximal balloon 4 through an opening 7 provided in the wall of the catheter. Alongside opening 7, a second opening 8 leading into balloon 4 exists in the wall of part 1 from which a connecting channel 9 (shown in dotted lines) also runs through the catheter wall to the middle balloon 5 and ends there in an opening 10 which has a significantly smaller cross-section than the openings 7 and 8 of proximal balloon 4. As a result, filling of balloon 5 is delayed compared with balloon 4 when a fluid (e.g. water) is admitted to balloon 4 via channel 6.

Near the distal end of catheter part 1 is a third balloon 11 connected to the wall of part 1. The opening 12 in the catheter wall connects this balloon 11 via a proximal channel 13 running through the catheter wall and an opening 14 at the proximal end of the catheter 3 with a small semi-balloon 15 permanently connected to the wall of part 1 which forms the main component of an opening mechanism of the valve opening 16. The valve opening 16 is defined by sealing lips produced by a diagonal cut in the wall of the proximal end of the catheter 3 which are pressed together and when closed are pressed even tighter together by the pressure inside the bladder.

The distal catheter part 2 is pushed onto catheter part 1. Two small-bore plastic pipes 17 and 18 serve as connecting elements. In addition, the small plastic pipe 17 links the longitudinal channel 6 with an elastic "puncture valve" 19 in front end of catheter part 2. The small plastic pipe 18 extends along a portion of longitudinal channel 13 running from a puncture valve 20 in the front end of catheter part 2 which runs in the wall of part 2 and ends in an opening 21 inside the balloon 11. Two loose threads 22 (one thread is not shown), one end of which is anchored in the wall of the disconnectable distal part 2 and the other end in the wall of the proximal part 1, create an additional loose connection between the two catheter parts 1 and 2. Proximally to the distal balloon 11, the catheter wall of part 1 has one or two relatively large openings 23 to drain the secretion from the proximal urethra into the lumen 24 of the catheter.

As can be more clearly seen in FIG. 9 and is not shown in FIGS. 1 and 2 for the sake of clarity, a thread 52 is securely anchored to the distal end of catheter part 2 and runs cross-wise across its lumen. This thread 52 serves, as explained in more detail further below, to insert the catheter to which the invention relates into and to extract the catheter from the urethra.

In accordance with FIG. 2, the female device to which the invention relates consists of a hose-like or tubular catheter, e.g. of silicone, the length of which is so dimensioned that in its inserted condition its distal end 28 lies within the female urethra 38 (FIG. 7) while its proximal end 3 extends into the lumen of the urinary bladder 39. The catheter consists of two disconnectable parts, a proximal part 25 and a distal part 26.

A first balloon 4 is permanently attached to the outside of the proximal part 25. From the distal end 28 of the distal catheter part 26, a channel 6 runs through the wall of part 26, continues through the wall of the proximal part 25 and enters the proximal balloon 4 through an opening 7 provided in the wall of catheter.

A second balloon 27 is permanently connected to the wall of the distal catheter part 26. The opening 12 in the catheter wall connects this balloon 27 via a channel 13 running through the catheter wall and an opening 14 at the proximal end 3 of the proximal catheter part 25 with a small semi-balloon 15 permanently connected to the wall of the catheter part 25 which forms the main component of an opening mechanism of the valve opening 16.

The distal catheter part 26 is pushed onto the proximal catheter part 25. Two small-bore plastic pipes 17 and 18 again serve as connecting elements. In addition, the small plastic pipe 17 links the longitudinal channel 6 with an elastic "puncture valve" 19 in front end of part 26. The small plastic pipe 18 extends along a longitudinal channel 13a running from a puncture valve 20 in the front end of catheter part 26 which ends in an opening 21 inside the balloon 27. Two loose threads 22 (one thread is not shown), one end of which is anchored in the wall of the distal catheter part 26 and the other end in the wall of the catheter part 25, create an additional loose connection between the two catheter parts 25 and 26.

In order to prevent a change in position of the incontinence catheter in the female urethra 38 when actuating the hydraulic release mechanism to open the valve opening 16 by compression of the balloon 27 which can be felt through the front vaginal wall 40 (FIG. 7), the balloon has between two and four strip-like, circular bulges or ribs 30 running transversely to the longitudinal axis of the incontinence catheter. The bulges 30 can also, if required, be replaced by other structures with the same function (not illustrated) which change the surface of the balloon 27. In the preferred embodiment, the surface of the balloon 27 has molded into the surface from two to four crosswise running ribs or batons number 30 in FIG. 2, or comparable retaining means, to prevent dislocation of the female incontinence catheter inside the short female urethra 38 when the balloon 27 is compressed according to FIG. 7. The ribs or comparable retaining means are molded into the exterior surface of the balloon to give the surface a rough texture to prevent dislocation in the urethra.

FIGS. 3, 4 and 5 show details and the function of the drain valve into the catheter lumen located at the proximal catheter end 3 which is the same in both the male and female incontinence catheters to which the invention relates.

Embedded in the wall of the proximal catheter end 3 under the pretension closing valve 16 is a resilient elastic baton of metal or plastic 32 running in longitudinal direction which is fitted in its position through an opening 31. Two threads 33 are tied around the two ends of baton 32 which fasten a roughly diamond-shaped piece of fleece 74 made from a human tissue-compatible material flat over the catheter end 3 and the semi-balloon 15. The fleece 74 is wider at its longitudinal centerline in order to prevent it slipping off the semi-balloon 15 during its subsequent expansion which is described below. As a fluid (e.g. water) is admitted under pressure via the channel 13 in the wall of the device and through the opening 14 into the semi-balloon 15, the small semi-balloon 15 is filled and thus expands.

When pressure is applied to the balloon 11 of the male device in accordance with FIG. 1 which can be felt through the wall of the male urethra 34 (FIG. 6) or when pressure is applied to the balloon 27 of the female device in accordance with FIG. 2 which can be felt through the front wall of the vagina 40 (FIG. 7) and through the wall of the female urethra 38, the pressure of the fluid (e.g. water) in channel 13 of the male or female device increases.

As a result of this increase in pressure, the semi-balloon 15 bulges and the more or less non-elastic fleece 74 covering the small semi-balloon 15 causes traction to be applied to the two threads 33 attached to the ends of the flexible baton 32 so that the plastic baton bends towards the small semi-balloon 15 like a hunting bow together with the wall of the proximal end 3 of the catheter. At the same time, the valve 16 on the opposite side of the proximal catheter end 3 opens, rather like the face mask of a knight's helmet from the Middle Ages, and allows the urine to flow in from the urinary bladder 35 or 39. When the urinary bladder 35 or 39 is empty and the pressure on the balloon 11 (FIG. 1) or 27 (FIG. 2) is relieved, the small semi-balloon 15 is emptied by the fluid (e.g. water) flowing back via channel 13 into the balloon 11 or 27. This is effected in particular by the elastic resilience of the elastic baton 32 as the bending strain in the baton is relieved and it returns to its original shape. The proximal catheter end 3 thus returns to its original form and the valve 16 is closed under the pressure exerted by the baton 32.

FIG. 6 shows a schematic view of the anatomy of the male urethra 34 with a full urinary bladder 35 with the male device in accordance with FIG. 1 inserted into the male urethra 34, whereby the valve opening 16 extending into the urinary bladder is closed. The balloon 11 used for the hydraulic opening of the valve opening 16 lies roughly at the level of the scrotum root 36. The urinary bladder sealing balloons 4 and 5 of the device are shown in filled condition above and below the area of the sphincter muscle 37.

FIG. 7 shows a schematic view of the anatomy of the female urethra 38 with a full urinary bladder 39 with the female device in accordance with FIG. 2 inserted into the female urethra 38. The proximal part 25 of the device (FIG. 2) with the sealing balloon 4 and the proximal end 3 extending into the full urinary bladder. The index finger 41 inserted into the outer opening of the vagina 40 compresses the balloon 27 of the device which can be felt through the front wall of the vagina 40 and the rear wall of the urethra 38, whereby the symphysis 42 (which is part of the bones of the pelvis) serves as an abutment for the pressure. The semi-balloon 15 of the proximal catheter end 3 thus bulges and the valve 16 is opened so that the urine can flow into the lumen of the device in the direction of the arrow.

FIG. 8 shows a schematic view of the male device just inserted into the male urethra 34 (but not yet secured in place) with a special rigid or partially elastic, sterile fitted filling and insertion rod 43, whereby the proximal end 3 extends into the urinary bladder 35 with the empty semi-balloon 15 and thus closed valve 16. The sealing balloon 4 of the proximal part 1 has already been filled with fluid (e.g. water) using a syringe 45 fitted into the valve 44 of the insertion rod 43 which corresponds to a prior art catheter valve. The second sealing balloon 5 of the proximal catheter section 1 has not yet been expanded.

A possible simpler design variant of the male device is indicated; this consists in the balloon 4 and balloon 5 being linked in a straight line by a single channel 6 already existing in the wall of the device, thus eliminating channel 9 (FIG. 1), whereby the single opening 7 in the catheter wall inside the balloon 4 has a significantly larger cross-section than an opening 10 of the balloon 5 connected to channel 6 so that after filling balloon 4, a short time remains to allow the device to be adjusted to the proper position by pulling it back slightly with slight tension on the insertion rod 43. This adjustment can be accomplished because the second balloon 5 fills more slowly than balloon 4.

The balloon 4 is thus positioned above the natural constriction of the urethra 34 in the area of the sphincter muscle 37 which still exists even in incontinent persons. Only then is the balloon 5 slowly filled with fluid (e.g. water), as shown in the design in FIG. 1, through the throttling effect of opening 10. The additional wall opening 8 within the balloon 4 and the corresponding channel 9 shown in FIG. 1 do not exist here.

When the device has been correctly positioned in the male urethra 34 as described, balloon 11 is filled with a few milliliters of fluid (e.g. water) with the help of a syringe 46 which is attached to a valve 47 on the insertion rod; this valve is identical with the valve 44. In order to avoid a simultaneous maximum filling of the semi-balloon 15 at the proximal end of the device, the openings 21 and 12 in the wall of the proximal catheter section 1 inside the balloon 11 can have different cross-sections such that opening 12 has a slightly smaller cross-section than opening 21.

FIG. 9 shows a schematic partial view of the distal section of the male incontinence catheter in accordance with FIG. 1 in the male urethra 34 at the moment of disconnection of the insertion rod 43 from the distal section 2 of the incontinence catheter after the balloons 4, 5 and 11 (FIG. 8 and FIG. 1) have already been filled by injection of fluid (e.g. water) via the valves 44 and 47 through cannula-like, round-tipped continuations 48 and 49 of the insertion rod 43 and through the elastic puncture valves or ball valves 19 and 20 in the distal section 2 of the device. (Balloons 4 and 5 not shown)

Inside the insertion rod 43 is a longitudinally shiftable rigid nucleus 50, the front end 50b of which can be inserted into the lumen of the catheter far enough that it passes over the joint between parts 1 and 2 (shown as a dotted line in FIG. 9) so that the joint is stabilized and the small pipes 17, 18 are protected from bending when the catheter is inserted. In the embodiment, the front end section 50b has a semi-circular cross-section in order to be able to pass the thread 52 running cross-wise through the lumen of the distal part 2 of the device and securely anchored to the wall of the distal part 2 of the device. At the rear end of the end section of 50b, the resulting rod shoulder has a notch 51 which holds the thread 52. A dislocation of the device during the extraction of the insertion rod 43 due to the adhesion of the cannulas 48 and 49 of the insertion rod 43 in the puncture valves 19 and 20 necessary at the start of positioning of the device in the male urethra 34 is avoided by exerting slight pressure on the outer end 50a of the nucleus 50.

Positioning of the female incontinence catheter in accordance with FIG. 2 in the female urethra 38 (FIG. 7) is performed in the same way (not illustrated) using an identical or slightly shorter insertion rod 43 in accordance with FIG. 8.

FIGS. 10 and 11 show schematic partial views of the male incontinence catheter in accordance with FIG. 1 during the process of removal from the male urethra 34. A special rigid or partially elastic sterile extraction rod 53 with its harpoon-like rounded tip 54 is first inserted blindly into the male urethra 34 and then pushed forward into the open lumen 24 of the distal part 2 of the device. When the extraction rod 53 is then pulled back, at least one but preferably two rounded barbs 55 of the tip 54 catches in the thread 52 running cross-wise through the lumen of the distal part 2 and is securely anchored in its walls. Further removal of the extraction rod 53 (the removal direction is indicated by an arrow in FIG. 11) causes the distal part 2 to be disconnected from the proximal part 1 of the device. The two small plastic pipes 17 and 18 are removed from the lumina of the wall channels 6 and 13. The balloons 4, 5 and 11 can empty via the free openings of the channels 6 and 13 in the wall of the proximal part 1 of the device into the lumen of the urethra 34 (indicated by arrows). The two threads 22 which are firmly anchored in the walls of parts 1 and 2 hold parts 1 and 2 together. The whole catheter can now be easily extracted from the male urethra 34 by further traction on the extraction rod 53.

FIG. 12 shows a schematic partial view of the female incontinence catheter in accordance with FIG. 2 during the process of removal from the female urethra 38. The extraction rod 53 is fundamentally identical with or shorter than that shown in FIGS. 10 and 11. When this extraction rod 53 is inserted into the female urethra 38 and then pushed forward into the open lumen 24 of the distal part 26 of the device, the rounded barbs 55 of the harpoon-like tip 54 of the extraction rod 53 catch in the thread 52 in the lumen 24 of the distal part 26. Further removal of the extraction rod 53 separates the distal part 26 from the proximal part 25. The two fluid-filled balloons 27 and 4 respectively empty via the small plastic pipe 18 forming part of the wall channel 13 which is securely attached to part 26 of the device and via the then open lumen of the wall channel 6 in the proximal part 25 of the catheter (indicated by arrows) into the female urethra 38. Further traction on the extraction rod 53 (the direction of the traction is indicated by an arrow) removes the female incontinence catheter from the female urethra 38.

In principle, the process of extraction of the male incontinence catheter in accordance with FIG. 1 from the male urethra 34, FIGS. 10 and 11, and of the female incontinence catheter in accordance with FIG. 2 from the female urethra 38, FIG. 12, can also be performed visually through a cystoscope using a conventional urethra foreign body forceps.

The emptying of the balloons 4, 5 and 11 or 4 and 27 necessary for the extraction is also possible via a modified construction which is not illustrated in the drawings.

With this construction it is planned that the corresponding channels 6 or 13 are each accessible via a "window" facing towards the lumen of the catheter, expediently mounted on the distal end of the catheter, which can be deliberately destroyed for the purpose of extraction. This window can be an opening closed off by a membrane until it is destroyed by means of a probe or urethra foreign-body forceps.

It is also within the spirit and scope of the present invention to deviate from the embodiments described above. For example, the invention is not limited to the form of the valve 16 produced by a diagonal cut at the catheter end 3. In principle, any type of valve is conceivable which opens up an inlet opening at the catheter end 3 by hydraulic actuation. Furthermore it could be considered protecting the fleece 74 which serves as a transmission element for opening the valve 16 by bending the resilient elastic baton 32 by means of a membrane or similar structure against the negative effects of the urine. Such a membrane can more or less surround the catheter end 3 in the area of the fleece 74, but without having a mechanical reaction on it. Instead of the fleece 74, any surgical material can be used which is capable of transmitting a tractive force to the resilient elastic baton 32 with no noticeable elastic expansion.

Furthermore, it is not absolutely essential to fill the actuating balloon 11 or 27, with which the semi-balloon 15 of the actuating mechanism is caused to bulge, with fluid only after insertion of the catheter. Instead the fluid can be contained from the outset in the closed-center system formed by the actuating balloon 11 or 27, the channel 13 and the semi-balloon 15.

In an alternative embodiment of the invention, the male incontinence catheter which is very similar to the male incontinence catheter shown in FIGS. 1, 3, 4, 5, 6, 8, 9, 10 and 11, and the only difference is the nature and configuration of the catheter. All of the parts of the alternative embodiment of the male incontinence catheter are numbered correspondingly with 100 added to each number.

Referring to FIGS. 13, 14 and 15, there is shown at 100 an alternative embodiment of the invention male incontinence catheter which is made of elastic material, e.g. silicone or any other suitable material. The male catheter 100 has a generally hose-like or tubular shaped body which comprises an elongated proximal part 101 with a proximal end 103 and a short distal part 102 with a distal end 198. The distal part 102 has a front section 130 and a rear section 132, where the two sections 130 and 132 are connected together by a pair of small plastic pipes 117 and 118 (or alternatively the pipes can be made out of any other suitable material). The front section 130 is pushed onto the rear section 132 such that the pair of plastic pipes 117 and 118 connect the two sections 130 and 132 together. The plastic pipe 117 links a longitudinal channel 106a with an elastic puncture valve or ball valve 119 at the distal end 198 of the catheter 100 while the other plastic pipe 118 extends a longitudinal channel 113a running from an elastic puncture valve or ball valve 120 in the distal end 198 of the catheter 100 which runs in the wall of the distal part 102 and terminates in an opening 121. The catheter 100 is provided with two loose threads 122 (only one is shown), where first ends are anchored in the wall of the front section 130 of the distal part 102 and the other ends are anchored in the wall of the rear section 132 of the distal part 102, and thereby create an additional loose connection between the two sections 130 and 132 of the distal part 102.

The length of the catheter 100 is so dimensioned that in the inserted condition, the distal part 102 lies within the male urethra 34 (see FIG. 6) while the proximal end 103 of the catheter 100 extends into the lumen of the urinary bladder 35 (see FIG. 6). The proximal part 101 is connected to the distal part 102 by a connecting bridge 196 which connects the two parts together. The connecting bridge 196 is inserted along a portion of proximal part 101 and along a portion of rear section 132 of distal part 102. The connecting bridge 196 can be made of plastic tubing material with higher rigidity than the proximal part 101 and the distal part 102, such as silicone material or any suitable material known to one skilled in the art so that it does not collapse when balloon 111 is operated. The connecting bridge 196 is attached to a portion of the proximal part 101 by adhesive means or a pressfit or any other suitable means known to one skilled in the art and the connecting bridge 196 is attached to a portion of the rear section 132 of distal part 102 by adhesive means, a pressfit or any other suitable means known to one skilled in the art.

Referring to FIGS. 13, 16, and 18, there is shown an upper retaining balloon 104 which is located adjacent to the proximal end 103 of the catheter 100. The upper retaining balloon 104 is permanently fixed to the exterior wall of the catheter proximal part 101. A short distance distally from the upper retaining balloon 104 is a smaller middle retaining balloon 105 which is also permanently fixed to the exterior wall of the catheter proximal part 101. An elongated channel 106 (shown as dashed lines) extends from opening 107 and proximal part 101 through the walls of proximal part 101, outside of connecting bridge 196 and into the wall of rear section 132 of distal part 102, and is connected to channel 106a by tubing 117. The channel 106 terminates inside the upper balloon 104 through the opening 107 which is provided in the wall of the catheter 100. A short connecting channel 109 (also shown as dashed lines) has two opposite openings 108 and 110, where the opening 108 is located adjacent to the opening 107. The connecting channel 109 is located on the interior wall of the catheter 100 and extends from the upper balloon 104 to the middle balloon 105, where the opening 108 communicates with the upper balloon 104 and the opening 110 communicates with the middle balloon 105. The opening 110 has a significantly smaller cross-section than the openings 107 and 108. As a result, the middle balloon 105 is filled more slowly than the upper balloon 104 when fluid (e.g. water) is entered through the upper balloon 104 via the channel 106. In a simplified version, it is possible to eliminate channel 109, where the smaller opening 110 is then situated in the channel 106 and as a result of that opening 107 being bigger than the opening 110, the middle balloon 105 is filled more slowly than the upper balloon 104.

Referring to FIGS. 13, 14 and 15, there is shown a compressible and non-expandable expandable actuating balloon 111 which is attached to a portion of the exterior wall of the proximal part 101 and to a portion of the exterior wall of the rear section 132 of distal part 102 of catheter 100. The actuating balloon 111 completely encloses the connecting bridge 196, which connecting bridge 196 interrupts the catheter tubing and allows for a greater working volume range for the balloon 111, which can be used for the operation of a tiny balloon 115. The compressible actuating balloon 111 creates more pressure than a silicone balloon because of its higher stiffness and its lower tendency to expand. The compressible actuating balloon 111 is made of Polyethyleneterephtalate (PET) material, silicon material or any other suitable material known to one skilled in the art. The tiny balloon 115 is made of elastic rubber like material such as silicone, latex, etc., so that it can expand when it is filled with fluid.

The upper balloon 104 has a fluid capacity of approximately 10 ccm while the middle balloon 105 has a fluid capacity of approximately 2–3 ccm. The actuating balloon 111 has a fluid capacity of approximately 2–3 ccm while the tiny balloon 115 has a capacity of approximately 0.5–1 ccm.

Referring to FIGS. 13, 14, 16, 17, and 18, a second longitudinal elongated channel 113 (also shown in dashed lines) is also provided with the catheter 100 and is located parallel to the first longitudinal channel 106. The second channel 113 has a first opening 112 which is in fluid communication with the actuating balloon 111. An opposite second opening 188 of the second channel 113 is connected to a non-elastic tubing such as a stainless steel tubing 190 (shown as dashed lines) which is glued, welded or molded together with the interior wall of the catheter 100, where the stainless steel tubing 190 is connected to the very tiny actuating balloon 115 located adjacent to the proximal end 103 of the catheter proximal part 101. The stainless steel tubing 190 allows a much easier handling of the tiny balloon 115 during production of the male incontinence catheter 100. The tiny balloon 115 forms the main component of an opening mechanism of a valve opening 116. A non-elastic strip 186 is attached to the exterior wall of the catheter 100 and holds the tiny balloon 115 in place. The non-elastic strip therefore will basically cause the tip of the catheter 103 to move away and open the valve 116 when the balloon 115 is filled with fluid. To ensure proper closure of the valve opening 116 with this embodiment, a small narrow strip of elastic material 184 such as silicone, rubber, etc., is attached under tension on the exterior wall of the catheter 100 and located on the same side as the valve opening 116. The strip of elastic material 184 is placed across the valve 116 to retain it in the closed position. Because of the tension on the elastic strip 184, the sealing lips of the valve opening 116 are pressed together, and thereby close reliably.

In an alternative embodiment which would eliminate the requirement to use the elastic strip 184 to close the valve 116, the non-elastic strip 186 is replaced by a plastic hinge-like material which causes an inward pressure against the balloon 115 and therefore forces the tip 103 of the catheter downward to cause the valve lips 116 to remain closed without the necessity of an elastic strip across them. One conceivable alternative arrangement of the non-elastic stripe 186 is to substitute in its place a plastic hinge which holds the valve opening 116 properly shut when the valve opening 116 is closed and additionally takes over the same functions as the previously discussed diamond shaped piece of fleece 74 for opening the valve 116. In another alternative arrangement, the plastic hinge 186 is replaced by a thin non-elastic film which prevents the balloon 115 from slipping off during its subsequent expansion and ensures the proper opening. To ensure a proper closure of the valve opening 116, a narrow elastic strip 184 such as silicone, rubber, etc., is attached under tension on the exterior wall of the catheter 100 and located on the same side as the valve opening 116 and crosses over the valve opening 116 to retain the valve shut in the closed position. Because of the tension on the elastic strip 184, the sealing lips of the valve opening 116 are pressed together, and thereby close reliably.

Referring to FIGS. 14, 16 and 18, located a short distance from the actuating balloon 111 is at least one relatively large opening 123 (only one is shown but preferably there are two oppositely disposed such openings) in the wall of the catheter proximal part 101 in order to facilitate the draining of secretion from the urethra into the lumen 124 of the catheter. At least two notch portions 152 or back-off clearances are provided within the catheter 100 and are integrally formed on opposite walls of the first section 130 of the distal part 102 adjacent distal end 198 of the catheter 100. These notch portions 152 serve to assist a user to insert the catheter 100 into and to extract the catheter 100 from the urethra 34 (see FIGS. 24 and 25).

Distal part 102 has a first channel 113a in first section 130 and an aligned second channel 113b in second section 132 which are connected by means of pipe 118. Second channel 113b ends in opening 121 while first channel 113a ends in puncture valve 120 or ball valve. Accordingly, when filling the device with fluid for purposes of expanding the tiny balloon 115, the fluid is inserted through puncture valve or ball valve 120 and flows through channels 113a and 113b into the volume of space occupied between connecting bridge 196 and balloon 111. Alternatively, the location between the connecting bridge 196 and balloon 111 can be pre-filled with fluid in the manufacturing process.

The actuating balloon 111, the tiny balloon 115, and the channel 113 are filled with fluid, e.g., water, but without pressure in the system. When pressure is applied to the actuating balloon 111 which can be felt through the wall of the male urethra 34 (FIG. 6), the pressure of the fluid in the channel 113 increases. As a result of this increase in pressure, the tiny balloon 115 expands and the strip or hinge 186 moves outwardly with the expansion of the balloon 115, thereby causing traction to be applied to the ends of the strip or hinge 186. At the same time, the valve opening 116 on the proximal end 103 of the catheter 100 opens, and allows the urine to flow into the lumen 124 from the urinary bladder 35. When the urinary bladder 35 is empty and the pressure on the actuating balloon 111 is removed, the tiny balloon 115 is emptied by the fluid flowing back via channel 113 and into the space between the actuating balloon 111 and the connecting bridge 196. This is effected in particular by the flexibility of the tiny balloon 115. The proximal end 103 of the catheter 100 returns to its original form and the valve opening 116 is closed under the pressure exerted by the elastic strip 184 or alternatively, by the use of the plastic hinge means which creates the inward pressure to close the valve opening 116. At this point in time, the entire hydraulic balloon system is again without pressure.

Referring to FIGS. 13 and 14, the male incontinence catheter 100 is installed by inserting it into the urethra 34 with the catheter not yet secured in position (see FIG. 8). The proximal end 103 extends into the urinary bladder 35 with the empty tiny balloon 115 and the valve opening 116 closed. The retaining balloon 104 has already been filled with fluid using a syringe 45 fitted to the valve 44 of an insertion rod 143 which corresponds to a prior art catheter valve (see FIG. 22), while the middle balloon 105 has not yet been expanded. The upper balloon 104 is thus positioned above the natural constriction of the urethra 34 in the area of the sphincter muscle 37 which still exists even in incontinent persons (see FIG. 6). Only then is the middle balloon 105 slowly filled with fluid, as shown in FIG. 13, through the throttling effect of the opening 110.

Figure 24:
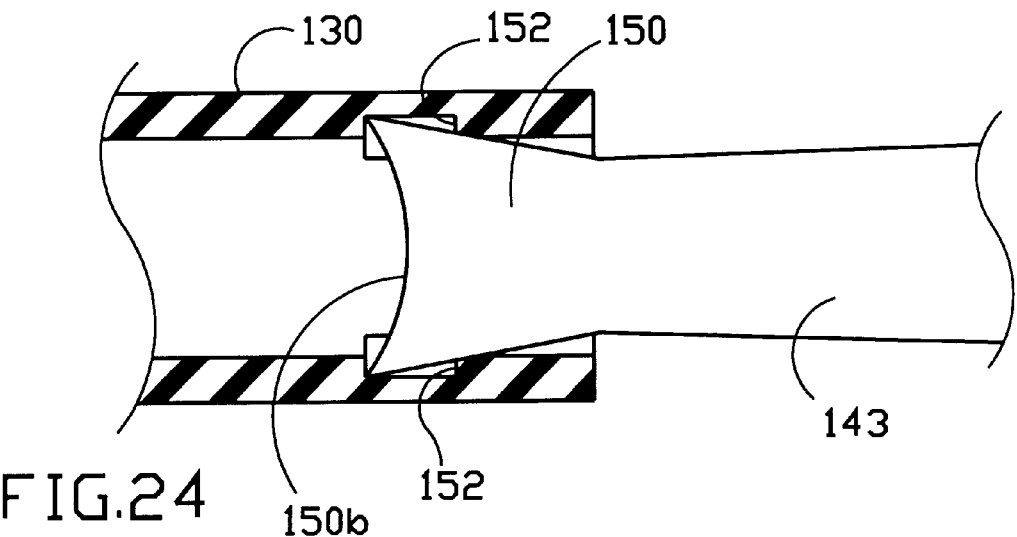
FIG. 24 is an enlarged fragmentary section of the distal part of the male or female incontinence catheter, showing the insertion rod inserted thereto.

Referring to FIG. 24, there is shown a partial view of the front section 130 of the male or female incontinence catheter. Inside the insertion rod 143 is a longitudinal, shiftable, rigid nucleus 150 which protrudes so far into the distal end of the catheter that the front and rear sections 130 and 132 (see FIG. 14) are stabilized and do not become disconnected when the catheter is inserted into the urethra. The proximal end 150b of the nucleus 150 has a semi-circular cross section which engages the notch portions 152 within the catheter to position the catheter within the urethra 34 (see FIG. 8). After the outer shell of the insertion rod 143 with its two cannulas 148 and 149 has been retracted slightly, the whole insertion rod 143 can be removed.

Figure 25:
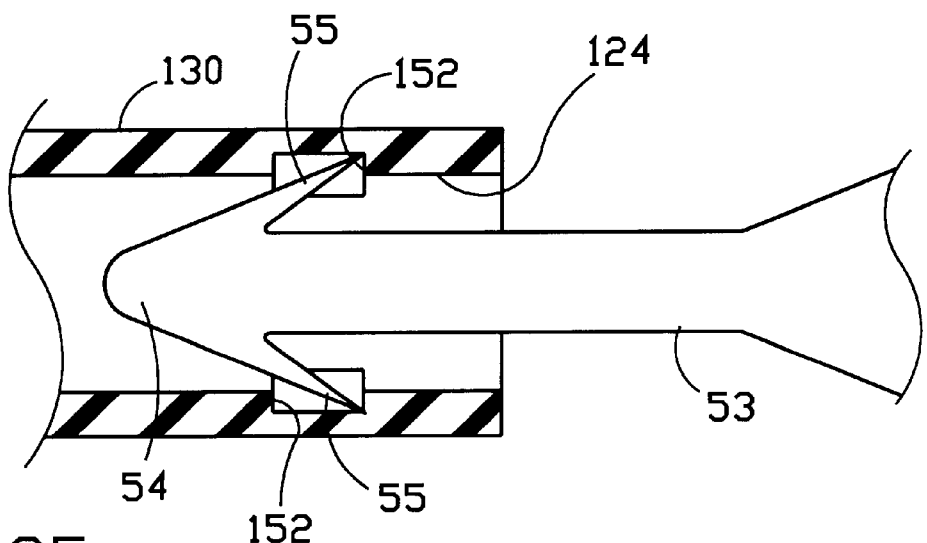
FIG. 25 is an enlarged fragmentary section of the distal part of the male or female incontinence catheter, showing the extraction rod inserted thereto.

Referring to FIGS. 13, 14 and 25, the male incontinence catheter 100 can be removed from the male urethra 34 by a special rigid or partially elastic sterile extraction rod 53 with its harpoon-like rounded tip 54, where the rod 53 is inserted blindly into the male urethra 34 and then pushed forward into the open lumen 124 of the distal part 102 of the catheter (see also FIGS. 10 and 11). When the extraction rod 53 is then pulled back, at least one, but preferably two or more rounded barbs 55 of the tip 54 catches on the notch portions 152 within the lumen 124 of the distal part 102. Further removal of the extraction rod 53 causes the front section 130 of the distal part 102 to be disconnected from the rear section 132 of the distal part 102 of the catheter 100. The two small plastic pipes 117 and 118 are retained in the lumen of the wall channels 106a and 113a. The balloons 104, 105 and 111 can be respectively emptied via the free openings of the channels 106 and 113b in the wall of the rear section 132 of the distal part 102 and empty in the urethra 34. The entire catheter 100 can now be easily extracted from the male urethra 34 by further traction on the extraction rod 53.

It will be appreciated that the present invention is not limited to the valve opening 116 which is formed by a diagonal cut at the proximal end 103 of the catheter 100. It is emphasized that while the diagonal valve opening 116 is preferred, it is also within the spirit and scope of the present invention to utilize any shape valve opening at the proximal end 103 of the catheter 100 which is actuated by a hydraulic actuation. The valve opening 116 is defined by sealing lips which are accomplished by a diagonal cut in the wall at the proximal end 103 of the catheter 100.

Referring to FIGS. 19, 20 and 21, there is shown another alternative embodiment of the invention male incontinence catheter 200 which is very similar to the embodiment just discussed and the only difference is the valve opening 216. Since it assembles and functions the same as previously described above except that an angled valve opening 216 is substituted for the diagonal valve opening 116 shown in FIGS. 13, 16 and 18, the description thereof will not be repeated. Only the modified components will be described in detail, and the parts are numbered correspondingly with 200 added to each number.

The valve opening 216 is defined by sealing lips produced by an angled cut in the wall at the proximal end 203 of the catheter 200. The angled valve 216 secures the valve lips from slipping off of each other. A small narrow elastic strip 284 (for example made of silicone or latex) may be utilized with this arrangement so that tension is provided to further assist in closing the valve opening 216 and located on the side of the valve opening 216.

As with the embodiment with the diagonal valve slit, the alternative arrangements of having a non-elastic strip over the balloon and having the hinge-like closure mechanism over the balloon still apply and function the same way as previously described for the other valve.

Referring to FIGS. 22 and 23, there is shown a female incontinence catheter 144 which is very similar to the male incontinence catheter 100 discussed above and shown in FIGS. 13, 14, 16, and 18. All of the parts of the female incontinence catheter 144 which are identical to the parts of the male incontinence catheter 100 are numbered with identical reference numerals.

The female catheter 144 has a generally tubular shaped body which is so dimensioned that in the inserted condition its distal end 128 lies within the female urethra 38 while its proximal end 103 extends into the lumen of the urinary bladder 39 (see FIG. 7). The female catheter 144 is put together by two disconnectable sections, including a proximal section 125 and a distal section 126. The distal section 126 has a front member 130 and a rear member 132, where the two members 130 and 132 are connected together by a connecting bridge 396 which is comparable to the one discussed above in the male incontinence catheter 100. However, in this embodiment, the connecting bridge connects the front member 130 of the distal section 126 to the rear member 132 of the distal section 126. Channel 106 extends on one portion from the proximal section 125 into opening 107 of balloon 104. Another portion of channel 106 extends from the portion of rear member 132 of distal section 126 adjacent proximal section 125 through the lower portion of the wall of rear member 132 outside the connecting bridge 396 and into the wall of first member 130 of distal section 126 and ending in puncture valve 119 located in channel 106 at distal surface 128 of first member 130 of distal section 126. The channel is brought together by means of plastic pipe 117 which is embedded in the portion of channel 106 which is in the wall of second member 132 of distal section 126. On the opposite side, channel 113 extends from proximal portion 125 into the opening to balloon 115 and extends into the lower surface of proximal section 125 adjacent second member 132 of distal section 126. An aligned channel 113b extends from the surface of second member 132 adjacent proximal section 125 to opening 112 on the distal surface of second member 132 of distal section 126. Plastic pipe 118 which is embedded in channel 1113b connects channel 113b to channel 113. While described as a plastic pipe, 117 and 118 can be a tubing made of any other suitable material such as metal, or any other material which is non-bendable and rigid. Finally, channel 113a extends across the dimension of first member 130 of distal section 126 from opening 121 at the proximal surface of distal section 126 to puncture valve or ball valve 120 located in channel 113a at the distal surface 128 of distal section 126.

The catheter proximal and distal sections 125 and 126 are connected together by pushing the proximal section 125 onto the distal section 126, where a pair of small bore plastic pipes 117 and 118 are provided to serve as connecting elements. Two loose threads 122 (only one is shown) are provided with the female incontinence catheter, where the first ends are anchored in the wall of the rear member 132 of the catheter distal section 126 and the other ends are anchored in the wall of the catheter proximal section 125, such that they create an additional loose connection between the two catheter sections 125 and 126.

A retaining balloon 104 is permanently attached to the exterior wall of the catheter proximal section 125. From the distal end 128 of the catheter 144, the channel 106 runs through the wall of the catheter distal section 126 and continues through the wall of the catheter proximal section 125 and enters the retaining balloon 104 through an opening 107 provided in the wall of the catheter 144.

A compressible and non-expandable actuating balloon 111 is attached to the exterior walls of the front and rear members 130 and 132 of the catheter distal section 126 and the balloon 111 surrounds connecting bridge 396. The actuating balloon 111 completely encloses the connecting bridge 396 which connecting bridge 396 interrupts the catheter tubing, and allows for a greater working volume range, which can be used for the operation of a very tiny actuating balloon 115. The actuating balloon 111 is identical to the one discussed above in the male incontinence catheter, and the description thereof will not be repeated.

The channel 113a has a first opening 112 located on the rear member 132 of the catheter distal section 126 and is in fluid communication with the actuating balloon 111. A second opening 188 on the channel 113 is connected to a rigid tubing 190 which can be made of stainless steel or other rigid material (shown as dashed lines) which is glued, welded or molded into channel 113, where the rigid tubing 190 is connected to the actuating balloon 115 located adjacent to the proximal end 103 of the catheter 144. The rigid tubing 190 allows a much easier handling of the tiny balloon 115 during production of the female incontinence catheter 144. The tiny balloon 115 forms the main component of an opening mechanism of a valve opening 116.

A non-elastic strip 186 is attached to the exterior wall of the catheter 144 and holds the tiny balloon 115 in place. The non-elastic strip therefore will basically cause the tip of the catheter 103 to move away and open the valve 116 when the balloon 115 is filled with fluid. To ensure proper closure of the valve opening 116 with this embodiment, a small narrow strip of elastic material 184 such as silicone, rubber, etc., is attached under tension on the exterior wall of the catheter 144 and located on the same side as the valve opening 116. The strip of elastic material 184 is placed across the valve 116 to retain it in the closed position. Because of the tension on the elastic strip 184, the sealing lips of the valve opening 116 are pressed together, and thereby close reliably.

In an alternative embodiment which would eliminate the requirement to use the elastic strip 184 to close the valve 116, the non-elastic strip 186 is replaced by a plastic hinge-like material which causes an inward pressure against the balloon 115 and therefore forces the tip 103 of the catheter downward to cause the valve lips 116 to remain closed without the necessity of an elastic strip across them. One conceivable alternative arrangement of the non-elastic strip 186 is to substitute in its place a plastic hinge which holds the valve opening 116 properly shut when the valve opening 116 is closed and takes over the same functions as the previously discussed diamond shaped piece of fleece 74 for opening the valve 116. In another alternative arrangement, the plastic hinge 186 is replaced by a thin non-elastic film which prevents the balloon 115 from slipping off during its subsequent expansion and ensures the proper opening. To ensure a proper closure of the valve opening 116, a narrow elastic strip 184 such as silicone, rubber, etc., is attached under tension on the exterior wall of the catheter 144 and located on the same side as the valve opening 116 and crosses over the valve opening 116 to retain the valve shut in the closed position. Because of the tension on the elastic strip 184, the sealing lips of the valve opening 116 are pressed together, and thereby close reliably.

Referring to FIGS. 22 and 23, there are at least two notch portions 152 or back-off clearances provided within the catheter 144 and are integrally formed on opposite walls of the first member 130 of the distal part 126 adjacent distal end 128 of the catheter 144. These notch portions 152 serve to assist a user to insert the catheter 144 into and to extract the catheter 144 from the urethra 38 (see FIGS. 12, 24 and 25).

When pressure is applied to the actuating balloon 111 which can be felt through the front wall of the vagina 40 (FIG. 7) and through the wall of the female urethra 38, the pressure of the fluid (example water) in the channel 113 increases. As a result of this increase in pressure, the tiny balloon 115 expands and the strip or hinge 186 moves outwardly with expansion of the balloon 115, thereby causing traction to be applied to the ends of the strip or hinge 186. At the same time, the valve opening 116 on the proximal end 103 of the catheter 144 opens, and allows the urine to flow into the lumen 124 from the urinary bladder 39. When the urinary bladder 39 is empty and the pressure on the actuating balloon 111 is removed, the tiny balloon 115 is emptied by the fluid flowing back via channel 113 and into the space between the actuating balloon 111 and the connecting bridge 396. This is effected in particular by the flexibility of the tiny balloon 115. The proximal end 103 of the catheter 144 returns to its original form and the valve opening 116 is closed under the pressure exerted by the elastic strip 184 or alternatively, by the use of the plastic hinge means which creates the inward pressure to close the valve opening 116. At this point in time, the entire hydraulic balloon system is again without pressure.

Referring to FIG. 24, there is shown a partial view of the front section 130 of the male or female incontinence catheter. Inside the insertion rod 143 is a longitudinal, shiftable, rigid nucleus 150 which protrudes so far into the distal end of the catheter that the front and rear sections 130 and 132 are stabilized and do not become disconnected when the catheter is inserted into the urethra. The proximal end 150b of the nucleus 150 has a semi-circular cross section which engages the notch portions 152 within the catheter to position the catheter within the urethra 38. After the outer shell of the insertion rod 143 with its two cannulas 148 and 149 has been retracted slightly, the whole insertion rod 143 can be removed.

Referring to FIGS. 22 and 25, during the process of removing the female incontinence catheter 144 from the female urethra 38, an extraction rod 53 is inserted into the female urethra 38 and then pushed forward into the open lumen 124 of the female catheter 144, the rounded barbs 55 of the harpoon-like tip 54 of the extraction rod 53 catch on the notch portions 152 within the lumen 124 of the front member 130 of the distal section 126 (see FIG. 25). Further removal of the extraction rod 53 separates the distal section 126 from the proximal section 125. The two fluid-filled balloons 111 and 104 empty via the small plastic pipes 117 and 118 and via the then open lumen of the wall channel 106 in the proximal section 125 of the catheter into the female urethra 38. Further traction on the extraction rod 53 removes the female incontinence catheter from the female urethra 38.

Defined in detail, the present invention is a device for treatment of human urinary incontinence to be used by a human being, comprising: (a) a longitudinal elongated catheter having a proximal part and a distal part, each part having a proximal end and a distal end, the catheter being installable within a urethra of the human being such that the proximal end of the proximal part extends into a bladder of the human being; (b) hollow connecting means connecting the proximal and distal parts of the catheter together and forming a gap between the distal end of the proximal part and the proximal end of the distal part; (c) a compressible lower balloon being actuated from outside of the urethra and integrally formed to the distal end of the proximal part and the proximal end of the distal part, and completely enclosing and sealing the gap to form a greater volume range to compress the compressible lower balloon, the compressible lower balloon filled with fluid thereto by a first channel running along the interior of the distal part of the catheter; (d) a flexible expandable and contractible middle balloon integrally formed with the exterior of the catheter at the proximal part for maintaining the position of the catheter within the urethra; (e) a flexible expandable and contractible upper balloon integrally formed with the exterior of the catheter at the proximal part and located adjacent to the proximal end for maintaining the position of the proximal end of the proximal part of the catheter within the bladder, the upper balloon being fillable with fluid by a second channel running along the interior of the distal and proximal parts of the catheter which in turn fills the middle balloon by a third channel connecting the upper balloon with the middle balloon, the upper balloon being larger than the middle balloon; (f) a valve formed on the proximal part of the catheter and located adjacent to the proximal end; (g) retaining means formed across the valve for further maintaining the valve closed; and (h) a hydraulic actuating mechanism having an expandable and contractible tiny balloon located on the proximal part of the catheter and adjacent to and on the opposite side of the valve, and traction means formed on the proximal part of the catheter and tightly covering the expandable and contractible tiny balloon, whereby when pressure is exerted on the lower balloon, the fluid from the lower balloon flows through a fourth channel running along the interior of the proximal part and connects the tiny balloon which in turn fills and expands against the traction means to move a portion of the catheter to open the valve while the catheter remains within the human being to permit urine to be discharged from the bladder, and when the pressure is removed from the lower balloon, the fluid flows back to the fourth channel into the lower balloon and thereby closes the valve after the urine has been evacuated from the bladder; (i) whereby said catheter remains in its inserted condition in the human being for the purposes of both closing off the flow of urine from the bladder and also permitting the urine to be evacuated from the bladder while the catheter remains in its inserted condition in the human being.

Defined broadly, the present invention is a device for treatment of human urinary incontinence to be used by a human being, comprising: (a) a catheter having a proximal part and a distal part, each part having a proximal end and a distal end, the catheter being installable within a urethra of the human being such that the proximal end of the proximal part extends into a bladder of the human being; (b) connecting means connecting the proximal and distal parts of the catheter together and forming a gap between the distal end of the proximal part and the proximal end of the distal part; (c) a compressible member attached to the distal end of the proximal part and the proximal end of the distal part, and completely enclosing and sealing the gap to form a greater volume range for compressing the compressible member, the compressible member being fillable with fluid thereto; (d) an expandable and contractible first member attached to the proximal part of the catheter for maintaining the position of the catheter within the urethra; (e) an expandable and contractible second member attached to the proximal part of the catheter and located adjacent to the proximal end for maintaining the position of the proximal end of the proximal part of the catheter within the bladder, the second member being fillable with fluid which in turn fills the first member; (f) a valve formed on the proximal part of the catheter and located adjacent to the proximal end; (g) retaining means formed across the valve for further maintaining the valve closed; and (h) an actuating mechanism having an expandable and contractible third member formed on the proximal part of the catheter and located adjacent to and on the opposite side the valve, and traction means formed on the proximal part of the catheter and tightly covering the expandable and contractible third member, whereby when pressure is exerted on the compressible member, the fluid from the compressible member flows to the third member which in turn fills and expands against the traction means to move a portion of the catheter to open the valve to permit urine to be discharged from the bladder, and when the pressure is removed from the compressible member, the fluid flows back into the lower balloon and thereby closes the valve after the urine has been evacuated from the bladder; (i) whereby said catheter remains in its inserted condition in the human being for the purposes of both closing off the flow of urine from the bladder and also permitting the urine to be evacuated from the bladder while the catheter remains in its inserted condition in the human being.

Defined more broadly, the present invention is a device for the treatment of human urinary incontinence to be used by a human being, comprising: (a) a catheter having a proximal part, a distal part and connecting means connecting the proximal part to the distal part together to form a gap therebetween, the catheter being installable within a urethra of the human being such that a proximal end of the proximal part extends into a bladder; (b) compressible means enclosing and sealing the gap to form a greater volume range for compressing the compressible means, the compressible means being fillable with fluid thereto; (c) expandable and contractible means attached to the catheter at the proximal part and located adjacent to the one end for maintaining the position of the one end of the proximal part of the catheter within the bladder, the expandable and contractible means being fillable with fluid thereto; (d) a valve formed on the proximal end of the proximal part of the catheter; (e) expandable and contractible actuating means attached to the proximal end of the proximal part of the catheter and located adjacent to and on the opposite side of the valve; and (f) traction means attached on the catheter and tightly covering the expandable and contractible actuating means, whereby when pressure is exerted on the compressible means, the fluid from the compressible means flows to the actuating means which in turn fills and expands against the traction means to move a portion of the catheter to open the valve to permit urine to be discharged from the bladder while the catheter remains within the human being, and when the pressure is removed from the compressible means, the fluid flows back into the compressible means and thereby closes the valve after the urine has been evacuated from the bladder; (g) whereby said catheter remains in its inserted condition in the human being for the purposes of both closing off the flow of urine from the bladder and also permitting the urine to be evacuated from the bladder while the catheter remains in its inserted condition in the human being.

Defined even broadly, the present invention is a device for the treatment of human urinary incontinence to be used by a human being, comprising: (a) a catheter having a proximal section with a proximal end, a distal section with a distal end, and connecting means connecting the proximal section with the distal section and forming a gap therebetween; (b) compressible means attached to the catheter and enclosing the gap to form a greater volume range for compressing the compressible means; (c) the catheter including a balloon arrangement which is filled with fluid to close off a bladder of the human being and to hold the catheter in the lumen of a urethra, the fluid being admitted to and discharged from the balloon arrangement through at least one channel which is closed off at the distal end of the catheter; (d) a valve formed on the proximal end of the catheter, whereby the length of the catheter is dimensioned such that its distal end lies within the urethra when the catheter is in the inserted condition and the proximal end lies within the lumen of the bladder, the valve actuated by pressure exerted from the outside of the urethra; and (e) an actuating mechanism mounted on the proximal end of the catheter such that the actuating mechanism is pressurized by pressure exerted on the compressible means for opening the valve to permit urine to be discharged from the bladder while the catheter remains within the human being and when pressure is removed from the compressible means, the valve closes after the urine has been evacuated from the bladder; (f) whereby said catheter remains in its inserted condition in the human being for the purposes of both closing off the flow of urine from the bladder and also permitting the urine to be evacuated from the bladder while the catheter remains in its inserted condition in the human being.

Further defined more broadly, the present invention is a device for the treatment of human urinary incontinence to be used by a person, comprising: (a) a catheter having a proximal section with a tip, a distal section, and connecting means connecting the proximal section with the distal section and forming a gap therebetween, the catheter being insertable into a urethra of the person and is dimensioned such that its distal section in the inserted condition lies within the urethra and its tip in the inserted condition lies within the bladder; (b) the catheter including a balloon arrangement which is filled with fluid to close off the urinary bladder and to hold the catheter in the lumen of the urethra, the fluid being admitted to and discharged from the balloon arrangement through at least one channel which is closed off at the opposite end of the tip of the proximal section; (c) a valve mounted adjacent to the tip of the catheter and which is positioned inside the bladder to permit urine to be evacuated when the valve is opened; and (d) means for covering the gap to form a greater volume range to open the valve to permit urine to be discharged from the bladder while the catheter remains within the person and means for closing the valve after the urine has been evacuated from the bladder; (e) whereby said catheter remains in its inserted condition in the person for the purposes of both closing off the flow of urine from the bladder and also permitting the urine to be evacuated from the bladder while the catheter remains in its inserted condition in the human being.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A device for treatment of human urinary incontinence to be used by a human being, comprising:
   a. a longitudinal elongated catheter having a proximal part and a distal part, each part having a proximal end and a distal end, the catheter being installable within a urethra of the human being such that the proximal end of the proximal part extends into a bladder of the human being;
   b. hollow connecting means connecting said proximal and distal parts of said catheter together and forming a gap between said distal end of said proximal part and said proximal end of said distal part;
   c. a compressible lower balloon being actuated from outside of the urethra and integrally formed to said distal end of said proximal part and said proximal end of said distal part, and completely enclosing and sealing said gap to form a greater volume range to compress the compressible lower balloon, the compressible lower balloon filled with fluid thereto by a first channel running along the interior of said distal part of said catheter;
   d. a flexible expandable and contractible middle balloon integrally formed with the exterior of said catheter at said proximal part for maintaining the position of said catheter within the urethra;
   e. a flexible expandable and contractible upper balloon integrally formed with the exterior of said catheter at said proximal part and located adjacent to said proximal end for maintaining the position of said proximal end of said proximal part of said catheter within the bladder, the upper balloon being fillable with fluid by a second channel running along the interior of said distal and proximal parts of said catheter which in turn fills said middle balloon by a third channel connecting the upper balloon with said middle balloon, the upper balloon being larger than said middle balloon;
   f. a valve formed on said proximal part of said catheter and located adjacent to said proximal end;
   g. retaining means formed across said valve for further maintaining said valve closed; and
   h. a hydraulic actuating mechanism having an expandable and contractible tiny balloon located on said proximal part of said catheter and adjacent to and on the opposite side of said valve, and traction means formed on said proximal part of said catheter and tightly covering the expandable and contractible tiny balloon, whereby when pressure is exerted on said lower balloon, the fluid from said lower balloon flows through a fourth channel running along the interior of said proximal part and connects the tiny balloon which in turn fills and expands against the traction means to move a portion of said catheter to open said valve while said catheter remains within said human being to permit urine to be discharged from the bladder, and when the pressure is removed from said lower balloon, the fluid flows back to the fourth channel into said lower balloon and thereby closes said valve after the urine has been evacuated from the bladder;
   i. whereby said catheter remains in its inserted condition in the human being for the purposes of both closing off the flow of urine from the bladder and also permitting the urine to be evacuated from the bladder while the catheter remains in its inserted condition in the human being.

2. The device in accordance with claim 1, further comprising a hooking element attached to the interior of said distal part of said catheter for assisting in the insertion and extraction of said device from the urethra.

3. The device in accordance with claim 2, wherein said hooking element is formed by a notch portion.

4. The device in accordance with claim 1, wherein said valve is formed by a diagonal cut on said proximal part of said catheter and having sealing lips for closing said valve.

5. The device in accordance with claim 1, wherein said valve is formed by an angled cut on said proximal part of said catheter and having upper and lower lips, where the upper lips are seated on the lower lips.

6. The device in accordance with claim 1, wherein said traction means is a non-elastic plastic strip, where ends are permanently fixed to said proximal part of said catheter.

7. The device in accordance with claim 1, wherein said hollow connecting mean is generally plastic tubing.

8. The device in accordance with claim 1, wherein said compressible lower balloon is made of silicon material.

9. A device for treatment of human urinary incontinence to be used by a human being, comprising:
   a. a catheter having a proximal part and a distal part, each part having a proximal end and a distal end, the catheter being installable within a urethra of the human being such that the proximal end of the proximal part extends into a bladder of the human being;
   b. connecting means connecting said proximal and distal parts of said catheter together and forming a gap between said distal end of said proximal part and said proximal end of said distal part;
   c. a compressible member attached to said distal end of said proximal part and said proximal end of said distal part, and completely enclosing and sealing said gap to form a greater volume range for compressing the compressible member, the compressible member being tillable with fluid thereto;
   d. an expandable and contractible first member attached to said proximal part of said catheter for maintaining the position of said catheter within the urethra;
   e. an expandable and contractible second member attached to said proximal part of said catheter and located adjacent to said proximal end for maintaining the position of said proximal end of said proximal part of said catheter within the bladder, the second member being fillable with fluid which in turn fills said first member;

f. a valve formed on said proximal part of said catheter and located adjacent to said proximal end;

g. retaining means formed across said valve for further maintaining said valve closed; and h. an actuating mechanism having an expandable and contractible third member formed on said proximal part of said catheter and located adjacent to and on the opposite side said valve, and traction means formed on said proximal part of said catheter and tightly covering the expandable and contractible third member, whereby when pressure is exerted on said compressible member from outside of the urethra, the fluid from said compressible member flows to the third member which in turn fills and expands against the traction means to move a portion of said catheter to open said valve to permit urine to be discharged from the bladder, and when the pressure is removed from said compressible member, the fluid flows back into said lower balloon and thereby closes said valve after the urine has been evacuated from the bladder;

i. whereby said catheter remains in its inserted condition in the human being for the purposes of both closing off the flow of urine from the bladder and also permitting the urine to be evacuated from the bladder while the catheter remains in its inserted condition in the human being.

10. The device in accordance with claim 9, further comprising a hooking element attached to the interior of said distal part of said catheter for assisting in the insertion and extraction of said device from the urethra.

11. The device in accordance with claim 10, wherein said hooking element is formed by a notch portion.

12. The device in accordance with claim 9, wherein said valve is formed by a diagonal cut on said proximal part of said catheter.

13. The device in accordance with claim 9, wherein said valve is formed by an angled cut on said proximal part of said catheter.

14. The device in accordance with claim 9, wherein said traction means is a non-elastic plastic strip.

15. The device in accordance with claim 9, wherein said connecting means is generally a plastic tubing.

16. The device in accordance with claim 9, wherein said compressible member is a balloon.

17. The device in accordance with claim 16, wherein said balloon is made of silicon material.

18. The device in accordance with claim 9, wherein said actuating mechanism is hydraulic.

19. A device for the treatment of human urinary incontinence to be used by a human being, comprising:

a. a catheter having a proximal part, a distal part and connecting means connecting the proximal part to the distal part together to form a gap therebetween, the catheter being installable within a urethra of the human being such that a proximal end of the proximal part extends into a bladder;

b. compressible means enclosing and sealing said gap to form a greater volume range for compressing the compressible means, the compressible means being fillable with fluid thereto;

c. expandable and contractible means attached to said catheter at said proximal part and located adjacent to said one end for maintaining the position of said one end of said proximal part of said catheter within the bladder, the expandable and contractible means being fillable with fluid thereto;

d. a valve formed on said proximal end of said proximal part of said catheter;

e. expandable and contractible actuating means attached to said proximal end of said proximal part of said catheter and located adjacent to and on the opposite side of said valve; and f. traction means attached on said catheter and tightly covering said expandable and contractible actuating means, whereby when pressure is exerted on said compressible means, the fluid from said compressible means flows to said actuating means which in turn fills and expands against the traction means to move a portion of said catheter to open said valve to permit urine to be discharged from the bladder while said catheter remains within the human being, and when the pressure is removed from said compressible means, the fluid flows back into said compressible means and thereby closes said valve after the urine has been evacuated from the bladder;

g. whereby said catheter remains in its inserted condition in the human being for the purposes of both closing of the flow of urine from the bladder and also permitting urine to be evacuated from the bladder while said catheter remains in its inserted condition.

20. The device in accordance with claim 19, wherein said an expandable and contractible means is a balloon.

21. The device in accordance with claim 20, wherein said balloon can be filled with fluid via a closed channel at one end of said distal part of said catheter.

22. The device in accordance with claim 21, wherein said channel is closed off by a ball valve.

23. The device in accordance with claim 19, further comprising a hooking element attached to the interior of said distal part of said catheter for assisting in the insertion and extraction of said device from the urethra.

24. The device in accordance with claim 23, wherein said hooking element is formed by a notch portion.

25. The device in accordance with claim 19, further comprising retaining means formed across said valve for further maintaining said valve closed.

26. The device in accordance with claim 19, further comprising an expandable and contractible middle balloon attached to said catheter and located between said expandable and contractible means and said compressible means for maintaining the position of said catheter within the urethra.

27. The device in accordance with claim 19, wherein said valve is formed by a diagonal cut on said one end of said proximal part of said catheter.

28. The device in accordance with claim 19, wherein said valve is formed by an angled cut on said one end of said proximal part of said catheter.

29. The device in accordance with claim 19, wherein said traction means is a non-elastic plastic strip, where ends of the plastic strip are permanently connected to said one end of said proximal part of said catheter for retaining said expandable and contractible actuating means in place.

30. The device in accordance with claim 19, wherein connecting means is generally a plastic tubing.

31. The device in accordance with claim 19, wherein said compressible means is a balloon.

32. The device in accordance with claim 31, wherein said balloon is made of silicon material.

33. A device for the treatment of human urinary incontinence to be used by a human being, comprising:

a. a catheter having a proximal section with a proximal end, a distal section with a distal end, and connecting means connecting the proximal section with the distal section and forming a gap therebetween;

b. compressible means attached to said catheter and enclosing said gap to form a greater volume range for compressing the compressible means;

c. said catheter including a balloon arrangement which is filled with fluid to close off a bladder of the human being and to hold the catheter in the lumen of a urethra, the fluid being admitted to and discharged from the balloon arrangement through at least one channel which is closed off at said distal end of said catheter;

d. a valve formed on said proximal end of said catheter, whereby the length of said catheter is dimensioned such that its distal end lies within the urethra when said catheter is in the inserted condition and said proximal end lies within the lumen of the bladder, the valve actuated by pressure exerted from the outside of the urethra; and e. an actuating mechanism mounted on said proximal end of said catheter such that the actuating mechanism is pressurized by pressure exerted on said compressible means for opening said valve to permit urine to be discharged from the bladder while said catheter remains within the human being and when pressure is removed from the compressible means, said valve closes after the urine has been evacuated from the bladder;

f. whereby said catheter remains in its inserted condition in the human being for the purposes of both closing of the flow of urine from the bladder and also permitting urine to be evacuated from the bladder while said catheter remains in its inserted condition.

34. The device in accordance with claim 33, further comprising a hooking element attached to the interior of said distal section of said catheter for assisting in the insertion and extraction of said catheter from the urethra.

35. The device in accordance with claim 34, wherein said hooking element is formed by a thread spanned transversely.

36. The device in accordance with claim 33, further comprising retaining means formed across said valve for further maintaining said valve closed.

37. The device in accordance with claim 36, wherein said retaining means is a narrow elastic strip.

38. A device for the treatment of human urinary incontinence to be used by a person, comprising:

a. a catheter having a proximal section with a tip, a distal section, and connecting means connecting the proximal section with the distal section and forming a gap therebetween, the catheter being insertable into a urethra of the person and is dimensioned such that its distal section in the inserted condition lies within the urethra and its tip in the inserted condition lies within the bladder;

b. said catheter including a balloon arrangement which is filled with fluid to close off the urinary bladder and to hold the catheter in the lumen of the urethra, the fluid being admitted to and discharged from the balloon arrangement through at least one channel which is closed off at the opposite end of said tip of said proximal section;

c. a valve mounted adjacent to said tip of said catheter and which is positioned inside the bladder to permit urine to be evacuated when the valve is opened; and d. means for covering said gap to form a greater volume range to open said valve to permit urine to be discharged from the bladder while said catheter remains within the person and means for closing said valve after the urine has been evacuated from the bladder;

e. whereby said catheter remains in its inserted condition in the person for the purposes of both closing of the flow of urine from the bladder and also permitting urine to be evacuated from the bladder while said catheter remains in its inserted condition.

39. The device in accordance with claim 38, wherein said valve is formed by a diagonal cut on said tip of said catheter.

40. The device in accordance with claim 38, wherein said valve is formed by an angled cut on said tip of said catheter.

41. The device in accordance with claim 38, wherein said connecting means is generally a plastic tubing.

42. The device in accordance with claim 38, wherein said covering means is a balloon.

43. The device in accordance with claim 42, wherein said balloon is made of silicon material.

\* \* \* \* \*